US009029168B2

(12) United States Patent
McAlpine et al.

(10) Patent No.: US 9,029,168 B2
(45) Date of Patent: May 12, 2015

(54) USE AND MAKING OF BIOSENSORS UTILIZING ANTIMICROBIAL PEPTIDES FOR HIGHLY SENSITIVE BIOLOGICAL MONITORING

(75) Inventors: Michael C. McAlpine, Lawrenceville, NJ (US); Manu Sebastian Mannoor, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 478 days.

(21) Appl. No.: 13/171,120

(22) Filed: Jun. 28, 2011

(65) Prior Publication Data

US 2012/0156688 A1 Jun. 21, 2012

Related U.S. Application Data

(60) Provisional application No. 61/359,070, filed on Jun. 28, 2010.

(51) Int. Cl.
*G01N 33/543* (2006.01)
*G01N 27/12* (2006.01)
*B82Y 15/00* (2011.01)
*B82Y 30/00* (2011.01)

(52) U.S. Cl.
CPC .............. *G01N 27/126* (2013.01); *B82Y 15/00* (2013.01); *B82Y 30/00* (2013.01)

(58) Field of Classification Search
CPC ...... G01N 27/126; B82Y 15/00; B82Y 30/00; A61B 5/1486; A61B 5/6801
USPC ........................................................ 436/518
See application file for complete search history.

(56) References Cited

U.S. PATENT DOCUMENTS

| 5,735,273 | A | * | 4/1998 | Kurnik et al. | ................. 600/345 |
| 6,103,033 | A | * | 8/2000 | Say et al. | ..................... 156/73.1 |
| 7,459,303 | B2 | * | 12/2008 | Wang et al. | ................ 435/287.1 |
| 7,828,728 | B2 | * | 11/2010 | Boock et al. | .................. 600/365 |

(Continued)

OTHER PUBLICATIONS

Beard-Pegler, M. A. et al., "Observations on the resistance to drying of staphylococcal strains.", J. Med. Microbiol., 1988, 26, pp. 251-255.

(Continued)

*Primary Examiner* — Melanie Y Brown
(74) *Attorney, Agent, or Firm* — Meagher Emanuel Laks Goldberg & Liao, LLP

(57) ABSTRACT

A biosensor and method of making are disclosed. The biosensor is configured to detect a target and may include a peptide immobilized on a sensing component, the sensing component having an anode and a cathode. The immobilized peptide may comprise an antimicrobial peptide binding motif for the target. The sensing component has an electrical conductivity that changes in response to binding of the immobilized peptide to the target. The immobilized peptide may bind one or more targets selected from the list consisting of: bacteria, Gram-negative bacteria, Gram-positive bacteria, pathogens, protozoa, fungi, viruses, and cancerous cells. The biosensor may have a display with a readout that is responsive to changes in electrical conductivity of the sensing component. The display unit may be wirelessly coupled to the sensing component. A resonant circuit with an inductive coil may be electrically coupled to the sensing component. A planar coil antenna may be disposed in proximity to the resonant circuit, the planar coil antenna being configured to provide power to the sensing component.

11 Claims, 22 Drawing Sheets

(56) References Cited

U.S. PATENT DOCUMENTS

| | | | |
|---|---|---|---|
| 2002/0049374 A1* | 4/2002 | Abreu | 600/405 |
| 2006/0206155 A1* | 9/2006 | Ben-David et al. | 607/9 |
| 2009/0010998 A1* | 1/2009 | Marchitto et al. | 424/449 |
| 2009/0093695 A1* | 4/2009 | Nakamura et al. | 600/347 |
| 2009/0250688 A1* | 10/2009 | Solomon et al. | 257/25 |
| 2011/0054583 A1* | 3/2011 | Litt et al. | 607/116 |

OTHER PUBLICATIONS

Beard-Pegler, M. A. et al., "Lysogenicity of methicillin-resistant strains of *Staphylococcus aureus*.", J. Med. Microbiol., 1985, 20, pp. 147-155.

Belgrader, P. et al., "PCR detection of bacteria in seven minutes.", Science, 1999, 284, pp. 449-450.

Chen, C. et al., "Performance of monolayer graphene nanomechanical resonators with electrical readout.", Nat. Nanotechnol., 2009, 4,pp. 861-867.

Chen, P. J. et al., "Microfabricated implantable parylene-based wireless passive intraocular pressure sensors.", J. Microelectromech. Syst., 2008, 17, pp. 1342-1351.

Choi, W. et al., "Synthesis of graphene and its applications: A review.", Crit. Rev. Solid State Mater. Sci., 2010, 35, pp. 52-71.

Cui, Y. et al., "Chemical functionalization of graphene enabled by phage displayed peptides.", Nano Lett., 2010, 10, pp. 4559-4565.

Dong, X. et al., "Electrical detection of DNA hybridization with single-base specificity using transistors based on CVD-grown graphene sheets.", Adv. Mat., 2010, 22, pp. 1649-1653.

Feng, L. et al., "A graphene functionalized electrochemical aptasensor for selective label-free detection of cancer cells.", Biomaterials, 2011, 32, pp. 2930-2937.

Ferrari, A. C. et al., "Raman spectrum of graphene and graphene layers.", Phys. Rev. Lett., 2006, 97.

Grayson, A. C. R. et al., A BioMEMS review: MEMS technology for physiologically integrated devices., Proc. IEEE, 2004, 92, pp. 6-21.

Kim, D. H. et al., "Dissolvable films of silk fibroin for ultrathin conformal bio-integrated electronics.", Nat. Mater, 2010, 9, pp. 511-517.

Kim, D. H. et al., "Silicon electronics on silk as a path to bioresorbable, implantable devices.", Appl. Phys. Lett., 2009, 95.

Kuang, Z. et al., "Biomimetic chemosensor: designing peptide recognition elements for surface functionalization of carbon nanotube field effect transistors.", ACS Nano, 2010, 4, pp. 452-458.

Kulagina, N. V. et al., "Antimicrobial peptide-based array for *Escherichia coli* and *Salmonella* screening." Anal. Chem. Acta., 2006, 575, pp. 9-15.

Kuzmych, O. et al., "Carbon nanotube sensors for exhaled breath components.", Nanotechnology, 2007, 18.

Li, Y. et al., "Multiplexed detection of pathogen DNA with DNA-based fluorescence nanobarcodes.", Nat. Biotechnol., 2005, 23, pp. 885-889.

Liao, L. et al., "High-speed graphene transistors with a self-aligned nanowire gate." Nature., 2010, 467, pp. 305-308.

Liu, Y. et al., "Biocompatible graphene oxide-based glucose biosensors.", Langmuir, 2010, 26, pp. 6158-6160.

Loh, K. J. et al., "Inductively coupled nanocomposite wireless strain and pH sensors.", Smart. Struct. Syst., 2008, 4, pp. 531-548.

Loh, K. J. et al., "Passive wireless sensing using SWNT-based multifunctional thin film patches.", Int. J. Appl. Electrom., 2008, 28, pp. 87-94.

Mannoor, M. S. et al., "Electrical detection of pathogenic bacteria via immobilized antimicrobial peptides.", Proc. Nat. Acad. Sci. U.S.A., 2010, 107, pp. 19207-19212.

Mohanty, N. et al., "Graphene-based single-bacterium resolution biodevice and DNA transistor: Interfacing graphene derivatives with nanoscale and microscale biocomponents.", Nano Lett., 2008, 8, pp. 4469-4476.

Neat, M. L. et al., ". Implantation of electrodes in the dentine of an upper canine tooth in the dog.", Br. J. Pharmacol., 1971, 43, pp. 476P-477P.

Ong, K. G. et al., "Design and application of a wireless, passive, resonant-circuit environmental monitoring sensor.", Sens. Actuat. A-Phys., 2001, 93, pp. 33-43.

Ong, K. G. et al., "Monitoring of bacteria growth using a wireless, remote query resonant-circuit sensor: Application to environmental sensing.", Biosens. Bioelectron., 2001, 16, pp. 305-312.

Pender, M. J. et al., "Peptide-mediated formation of single-wall carbon nanotube composites.", Nano Lett., 2006, 6, pp. 40-44.

Phillips, M., "Method for the collection and assay of volatile organic compounds in breath.", Anal. Biochem., 1997, 247, pp. 272-278.

Potyrailo, R. A. et al., "Multianalyte chemical identification and quantitation using a single radio frequency identification sensor.", Anal. Chem., 2007, 79, pp. 45-51.

Schedin, F. et al., "Detection of individual gas molecules adsorbed on graphene.", Nat. Mater., 2007, 6, pp. 652-655.

Service, R. F., "Can sensors make a home in the body?", Science, 2002, 297, pp. 962-963.

Solnick, J. V. et al., "Determination of the infectious dose of *Helicobacter pylori* during primary and secondary infection in rhesus monkeys (*Macaca mulatta*).", Infect. Immun., 2001, 69, pp. 6887-6892.

Staii, C., Johnson Jr. et al., "DNA-decorated carbon nanotubes for chemical sensing.", Nano Lett., 2005, 5, pp. 1774-1778.

Stojanovic, G. et al., "Monitoring of water content in building materials using a wireless passive sensor.", Sensors, 2010, 10, pp. 4270-4280.

Strand, N. et al., "Chemically Polymerized Polypyrrole for On-Chip Concentration of Volatile Breath Metabolites.", Sens. Actuators B. Chem., 2010, 143, pp. 516-523.

Timlin, J. A. et al., "Raman spectroscopic imaging markers for fatigue-related microdamage in bovine bone.", Anal. Chem., 2000, 72, pp. 2229-2236.

Vepari, C. et al., "Silk as a biomaterial.", Progress in Polymer Science (Oxford), 2007, 32, pp. 991-1007.

Yao, H. et al., "A contact lens with embedded sensor for monitoring tear glucose level.", Biosens. Bioelectron., 2011, 26, pp. 3290-3296.

Yang, W. et al., "Carbon nanomaterials in biosensors: Should you use nanotubes or graphene.", Angew. Chem. Int. Ed., 2010, 49, pp. 2114-2138.

Zasloff, M., "Antimicrobial peptides of multicellular organisms.", Nature, 2002, 415, pp. 389-395.

Zelada-Guillen, G. A. et al., "Immediate detection of living bacteria at ultralow concentrations using a carbon nanotube based potentiometric aptasensor.", Angew. Chem. Int. Ed., 2009, 48, pp. 7334-7337.

Zheng, G. et al., "Multiplexed electrical detection of cancer markers with nanowire sensor arrays.", Nat. Biotechnol., 2005, 23, pp. 1294-1301.

\* cited by examiner

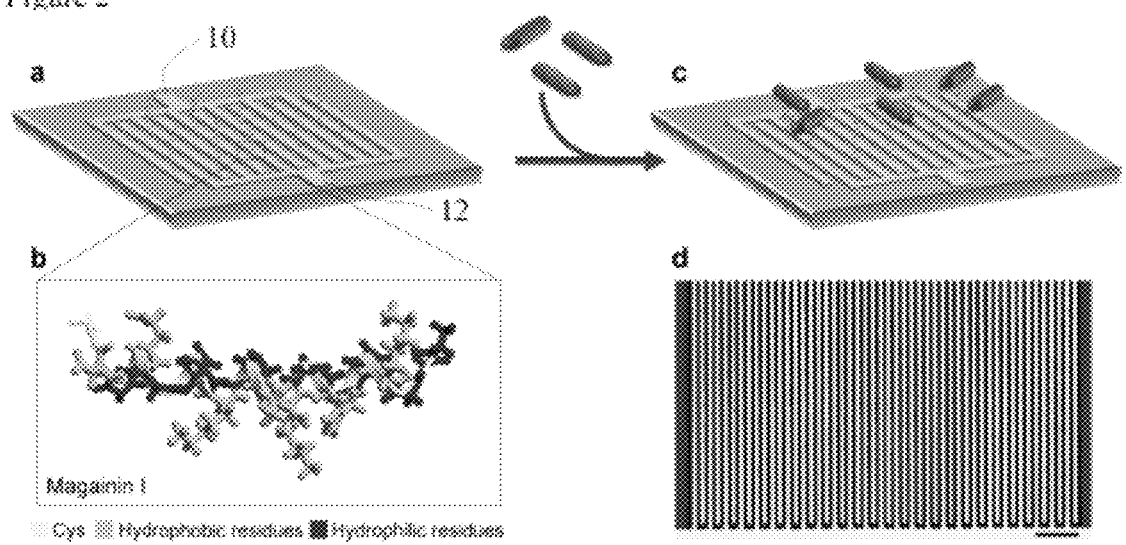

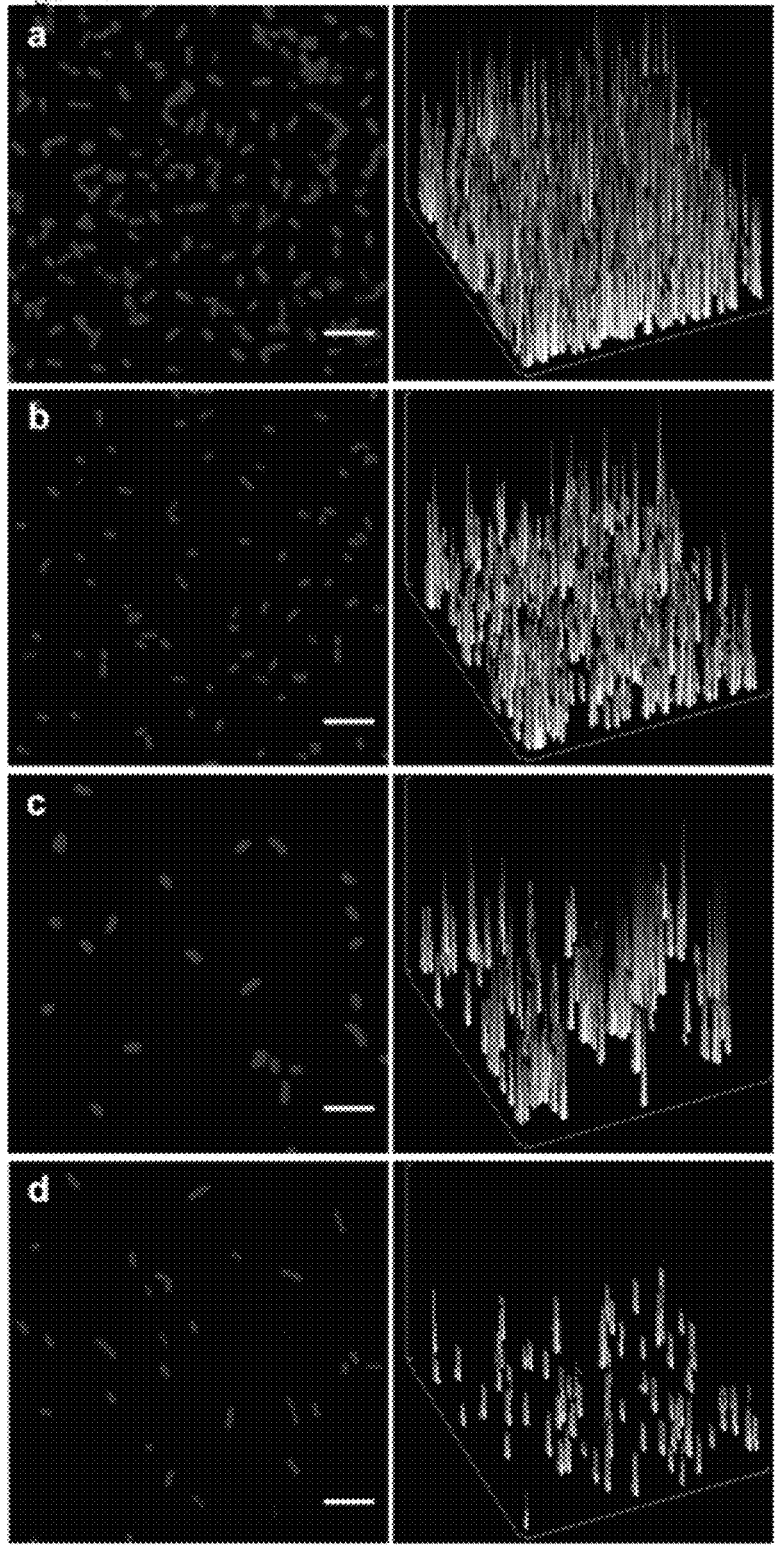

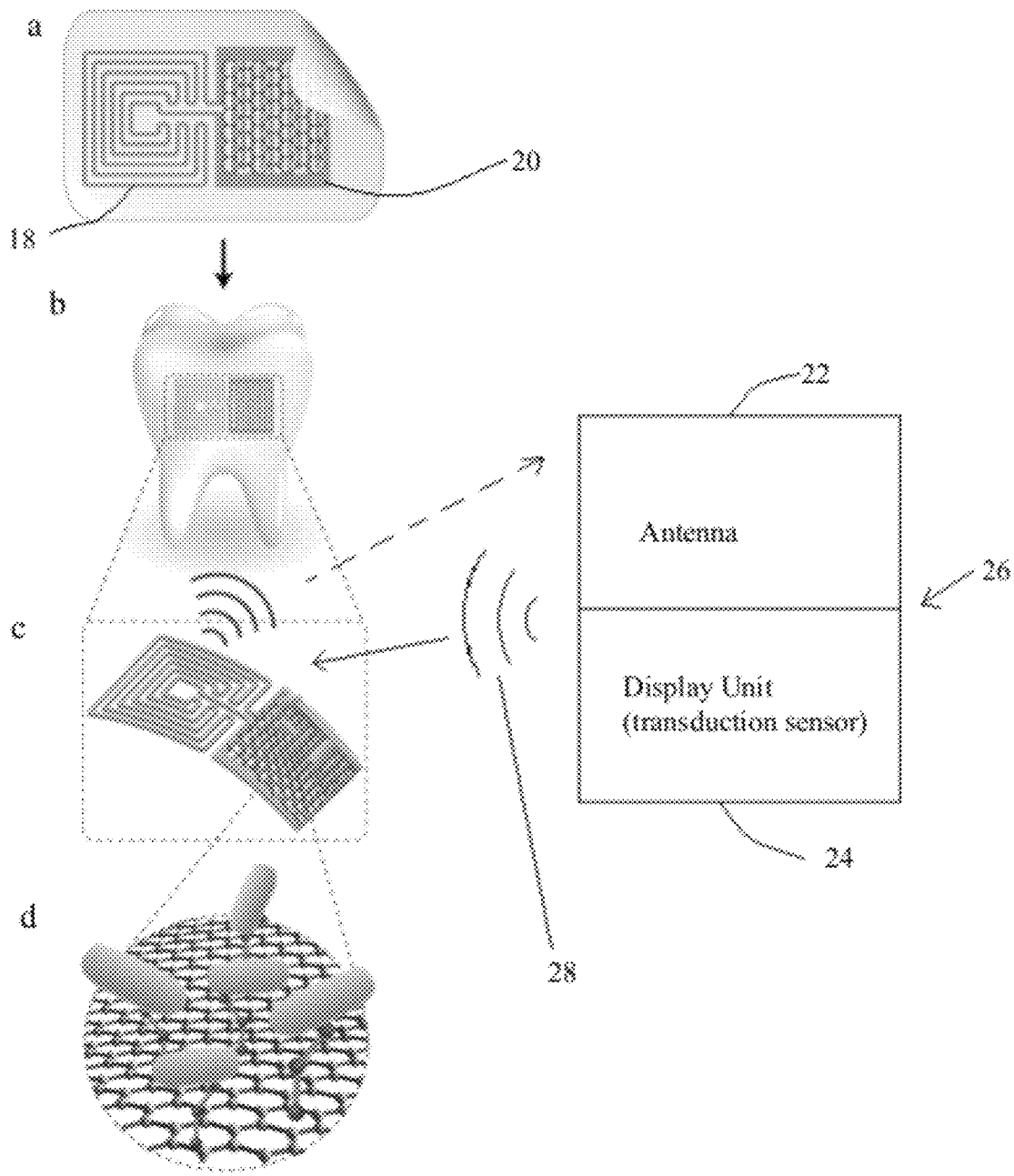

Figure 13
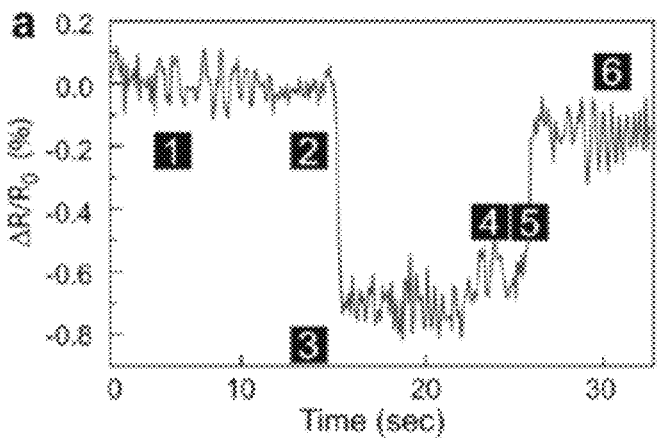
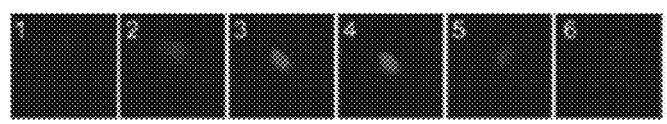
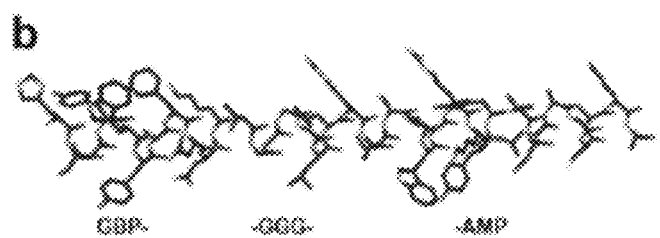
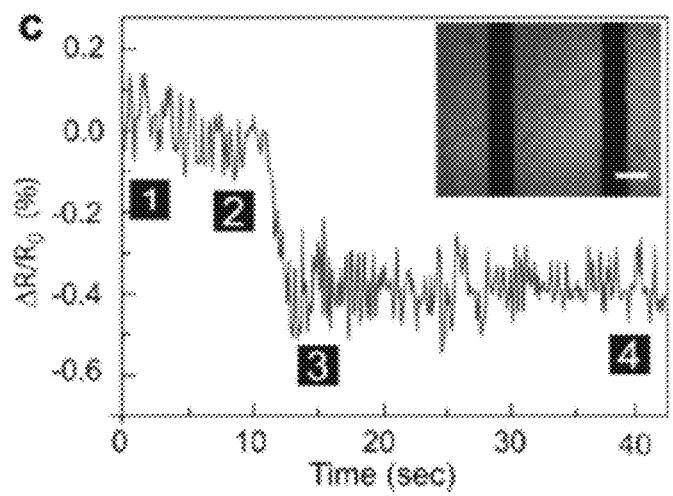
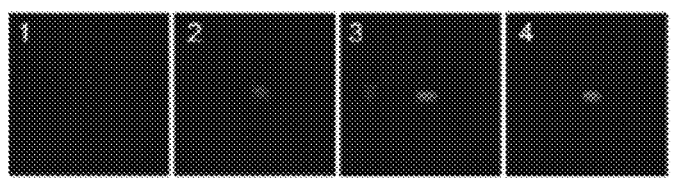

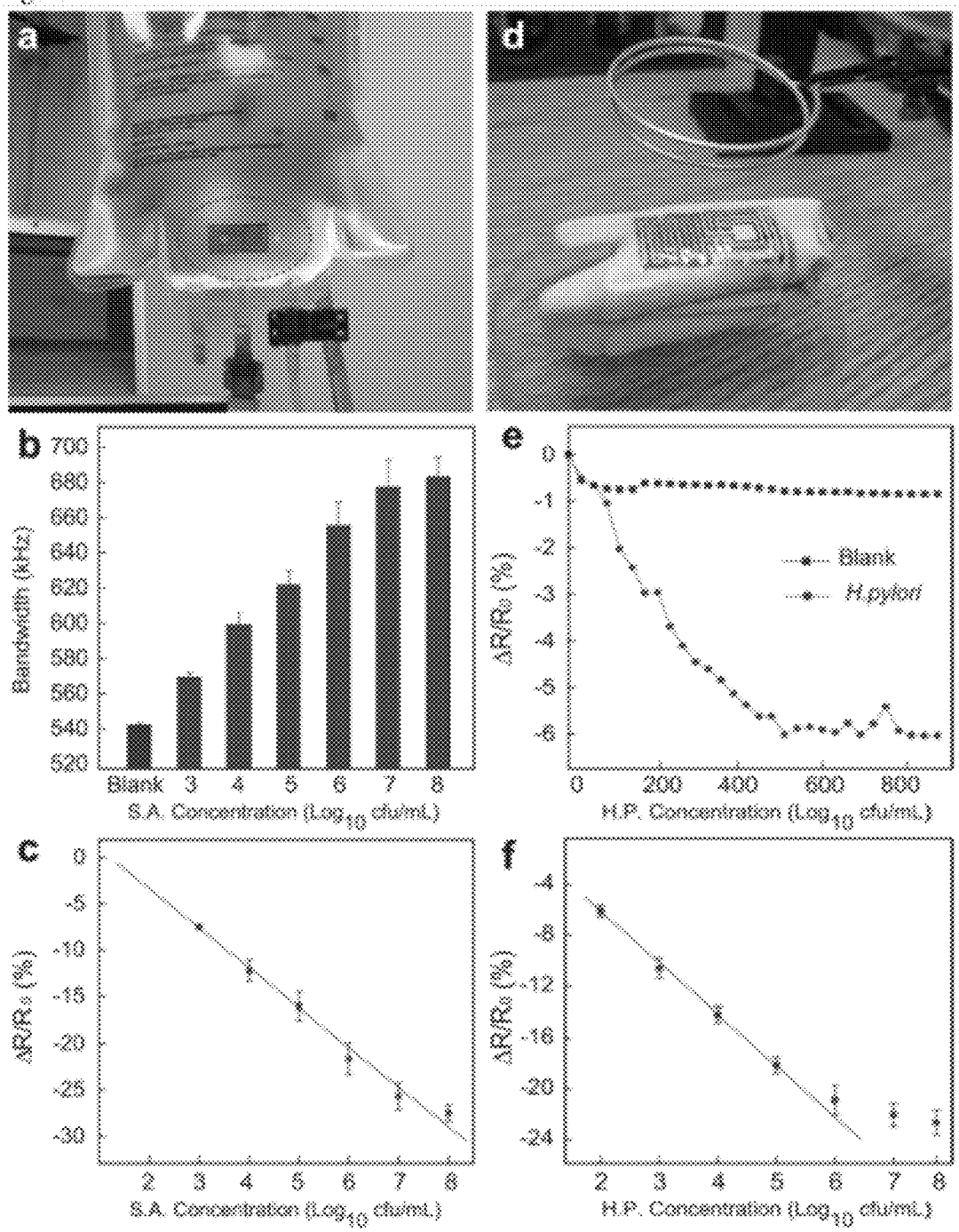

USE AND MAKING OF BIOSENSORS UTILIZING ANTIMICROBIAL PEPTIDES FOR HIGHLY SENSITIVE BIOLOGICAL MONITORING

CROSS-REFERENCE TO PRIOR FILED APPLICATION

This application claims priority to an earlier filed provisional application 61/359,070 filed on Jun. 28, 2010, which is herein incorporated by reference in its entirety.

UNITED STATES GOVERNMENT RIGHTS

This invention was made with government support under Air Force Office of Scientific Research via a Young Investigator Grant (#FA9550-09-1-0096) and as a fellow of the American Asthma Foundation (09-0038). The government has certain rights to this invention.

SEQUENCE LISTING

The instant application contains a Sequence Listing which has been submitted electronically in ASCII format and is hereby incorporated by reference in its entirety. Said ASCII copy, created on Feb. 5, 2015, is named PRINCETON-13702_SL.txt and is 9,507 bytes in size.

FIELD OF INVENTION

This invention relates to the field of biosensors; more specifically the invention related to the detection of Gram-negative, Gram-positive bacteria and other biologic targets through biosensors utilizing immobilized antimicrobial peptides. Certain embodiments of this invention also relate to the field of nanotechnology.

BACKGROUND

Bacterial infections remain the leading cause of death in developing nations, accounting for an estimated 40% of deaths (Ivnitski D et al. (1999) Biosens Bioelectron 14:599-624). For instance, the strain O157:H7 of *E. coli* is considered to be one of the most dangerous food borne pathogens (Buchanan R L, et al. (1997) Food Technol 51:69-76 and Jay J M ed. (1992) in Modern food microbiology. (Van Nostrand Reinhold, N.Y.)). In developed countries, bacterial contamination is also of critical concern, particularly in the pharmaceutical industry, where the most reliable test for contamination is the detection of endotoxins with horseshoe crab blood (Walls E A, Berkson J, Smith S A (2002) *Rev Fish Sci* 10:39-73). Microbial infections and drug-resistant supergerms are also a leading cause of military deaths, particularly in soldiers with burn injuries, and are considered potential biowarfare agents (Compton J A F (1987) in *Military chemical and biological agents: Chemical and toxicological properties*. (Telford press, Caldwell, N.J.) pp: 458, Malcolm D ed. (1994) in *Biological Warfare in the 21st Century*. (Brassey's, UK): 258, and D'Avignon L C, et al (Jan. 13, 2010) *Contribution of bacterial and viral infections to attributable mortality in patients with severe burns: An autopsy series*. Burns).

While containment strategies such as vaccination and "broadband" antibiotic usage in hospitals have helped reduce the severity of bacterial infections, these strategies have also inadvertently promoted the emergence of antibiotic resistance. Thus, the development of a sensor that can detect the presence of an infectious outbreak from a broad spectrum of pathogenic species would be desirable. It would be especially desirable if the sensor was scalable so that it could be used in nearly every situation where monitoring is desired, including the laboratory, in the field at the source of potential infection, and on or inside animals, including humans, that many be exposed to infection.

SUMMARY OF THE INVENTION

A biosensor and method of making are disclosed. The biosensor is configured to detect a target and may include a peptide immobilized on a sensing component, the sensing component having an anode and a cathode. The immobilized peptide may comprise an antimicrobial peptide binding motif for the target. The sensing component has an electrical conductivity that changes in response to binding of the immobilized peptide to the target. The target may be a bacterium, a Gram-negative bacterium, *Escherichia coli* and/or *Escherichia coli* O157:H7. The immobilized peptide may bind one or more targets selected from the list consisting of: bacteria, Gram-negative bacteria, Gram-positive bacteria, pathogens, protozoa, fungi, viruses, and cancerous cells.

The biosensor may have a display unit electrically coupled to the sensing component forming an electric circuit, the display unit having a readout that is responsive to changes in electrical conductivity of the sensing component. The display unit may be wirelessly coupled to the sensing component, the display unit having a readout that is responsive to changes in electrical conductivity of the sensing component. A power source may be electrically coupled to the sensing component. A wireless telemetry device may be electrically coupled to the sensing component. A resonant circuit with an inductive coil may be electrically coupled to the sensing component. A planar coil antenna may be disposed in proximity to the resonant circuit, the planar coil antenna being configured to provide power to the sensing component.

The sensing component may have a longest linear dimension of less than 1 mm. The sensing component may have a longest linear dimension of less than 1 μm. The display unit may use impedance spectroscopy to determine the electrical conductivity of the electric circuit and change the readout accordingly. The sensing component may be an interdigitated microelectrode array. The sensing component may be a graphene substrate. The sensing component may be a nanowire substrate.

A method of using an immobilized antimicrobial peptide to detect a target is disclosed, the method may include exposing the sample to at least one peptide immobilized on a sensing component, the immobilized peptide having an antimicrobial binding motif, the electrical conductivity of the sensing component changing in response to binding of the immobilized peptide with a target. The electrical conductivity of the sensing component is measured. The presence or absence of the target in the sample is determined based on the electrical conductivity of the sensing component. An electric circuit may be formed including the sensing component and a power source. The electric circuit may be powered with a planar coil antenna disposed in proximity to the electric circuit. A concentration of a target may be determined based on the electrical conductivity of the sensing component.

A method of making a biosensor configured to detect a target is disclosed. The method may include selecting an antimicrobial peptide based on its binding affinity for the target. The antimicrobial peptide may be immobilized on a sensing component, the sensing component having an electrical conductivity that changes based on binding to the target. An anode and a cathode are coupled to the sensing component. The antimicrobial peptide may be modified prior to being immobilized. The biosensor may be embedded on a bioresorbable substrate. The bioresorbable substrate may be selected from a list consisting of: poly(ethylene terepthalate), poly(imide), poly(ether sulfone), cellulose, paper, silk and silk fibroin.

The biosensor may include an antimicrobial peptide immobilized on a microbe, the microprobe having an electrical conductivity that is dependent on a binding state of the binding molecule. An anode and a cathode may be coupled to the microprobe. A display with a readout may be electrically coupled to the cathode and anode, forming a circuit, the readout being based on the electrical conductivity of the microprobe.

The biosensor may include an interdigitated microelectrode array disposed on a bioresorbable substrate. An anode and a cathode may be electrically coupled to the interdigitated microelectrode array. A resonant circuit with an inductive coil may be electrically coupled to the cathode and anode. A wireless telemetry unit may be electrically coupled to the resonant circuit, forming an electric circuit. A binding molecule may be disposed on the interdigitated microelectrode array, the interdigitated microelectrode having an electrical conductivity that is dependent on a binding state of the binding molecule. The binding molecule may be selected from the list consisting of: antimicrobial peptides, antibodies, modified antimicrobial peptides, modified antibodies, chimeric peptides containing antimicrobial peptide binding motifs, chimeric peptides containing antibody binding motifs, DNA fragments, RNA fragments, peptide binding motifs, proteins, small molecules and polymers combinations thereof. The bioresorbable substrate is selected from a list consisting of: poly(ethylene terepthalate), poly(imide), poly(ether sulfone), cellulose, paper, silk, silk fibroin and combinations thereof.

The bioresorbable substrate may be placed in contact with a biologic surface. The biologic surface may be capable of bioresorption. The biologic surface may be selected from the list consisting of: teeth, bone, skin, tissue, hair, nail, cornea, gum, tongue, palate, brain, heart, lung, membrane, leaf, root, bark, fur, feather, chiton and scale. The biosensor may also include a receiver unit having a planar coil antenna electrically coupled to a readout, the planar coil antenna being configured to power the electric circuit, enabling the wireless telemetry unit to send a wireless signal corresponding to an electrical conductivity of the circuit to the receiver unit, the readout being responsive to changes in the electrical conductivity of the circuit. The binding molecule may contain a glucose-binding motif.

BRIEF DESCRIPTION OF THE FIGURES

FIG. 2(A) depicts an artistic illustration of AMPs immobilized on an interdigitated microelectrode array;

FIG. 2(B) depicts a magnified artistic illustration image of the AMP magainin I in helical form, modified with a terminal cysteine residue, and with clearly defined hydrophobic and hydrophilic faces;

FIG. 2(C) depicts an artistic illustration of the detection of bacteria via binding of target cells to the immobilized AMPs;

FIG. 2(D) depicts an optical image of the interdigitated microelectrode array (scale bar: 50 µm);

FIGS. 6A-C depict the optical microscopy of the selectivity of AMPs, the left panels are pictures of selective binding of the immobilized AMP to various stained bacterial cells ($10^7$ cfu/mL), including: (A) $E.\ coli$ O157:H7, (B) $S.\ typhimurium$, (C) $E.\ coli$ ATCC 35218, and (D) $L.\ monocytogenes$, the right panels are graphs of the corresponding surface density of the bound cell, scale bars are 10 µm;

FIGS. 9A-F depicts an artistic illustration of the steps for transfer printing SNAP nanowires onto plastic substrates;

FIGS. 11A-D depict artistic illustrations of a graphene/silk-based bioresorbable passive wireless biosensor;

FIG. 11A depicts an artistic illustration of a graphene based wireless biosensor with a hybrid sensing element and a passive wireless telemetry system on a bioresorbable platform of silk fibroin;

FIG. 11B depicts an artistic illustration of the biosensor after bioresorption of the silk fibroin and the attachment of the biosensor on to the surface of a tooth;

FIG. 11C depicts a magnified artistic illustration of the bioresorbed sensing element, illustrating the capability of wireless remote query monitoring;

FIG. 11D depicts an artistic illustration of the recognition and binding of pathogenic bacterial cells by robust and naturally occurring antimicrobial peptide based biorecognition moieties assembled on the graphene nanomaterial transducer;

FIG. 12A depicts an image of a large area graphene nanotransducer transfer printed on to bioresorbable platform of silk fibroin FIG. 12B depicts an image of the passive wireless telemetry system consisting of a planar meander line inductor and interdigitated capacitive electrodes integrated on to the graphene/silk nanocomposite;

FIG. 12C depicts an image of a large area graphene transducer/gold electrodes bioresorbed on to the surface of human molar;

FIG. 12D depicts an image of a graphene based wireless element bioresorbed on to tissue;

FIG. 12E depicts a graph of the raman spectra of surface graphene integration;

FIG. 12F depicts a graph of the raman spectra of the graphene integrated on to the tooth surface through silk bioresorption;

FIGS. 13A-C collectively illustrate single bacterium detection using the biosensor;

FIG. 13A depicts, in the upper section, a graph of resistance data recorded during the binding and unbinding of single *E. coli* O:157 H7 bacterial cell over time on the graphene biosensor; the lower section shows simultaneous optical florescent photographs of the event;

FIG. 13B shows a schematic of a synthetized peptide consisting of a biocombinatorially derived graphene binding motif coupled to naturally occurring antimicrobial peptide (O-HP) based robust moieties a triglycine linker (-GGG-);

FIG. 13C depicts, in the upper section, a graph of resistance data recorded during the binding of single *E. coli* O:157 H7 bacterial cell over time on the graphene biosensor; the lower section shows simultaneous optical florescent photographs of the event;

FIGS. 14A-F depict the wireless remote monitoring of *S. aureus* and *H. pylori*;

FIG. 14A shows the optical image of graphene based wireless sensor integrated on to the surface of an I.V. bag;

FIG. 14B depicts a bar graph of the bandwidth the sensor resonance corresponding to various concentrations of the *S. aureus* cells incubated on the biosensor surface and dried;

FIG. 14C depicts a line graph of the percentage change in graphene resistance versus log of concentration of *S. aureus*;

FIG. 14D depicts an optical image of the graphene based wireless sensor bioresorbed on to the surface of a bovine tooth;

FIG. 14E depicts a line graph of the percentage change in graphene resistance versus time up on the exposure of a sample of 100 cells per µL *H. pylori* in DI water; and FIG. 14F depicts a line graph of the percentage change in graphene resistance versus log of concentration of *H. pylori*; error bars show standard deviation (N=3).

DETAILED DESCRIPTION OF THE INVENTION

Definitions

Figure 1:
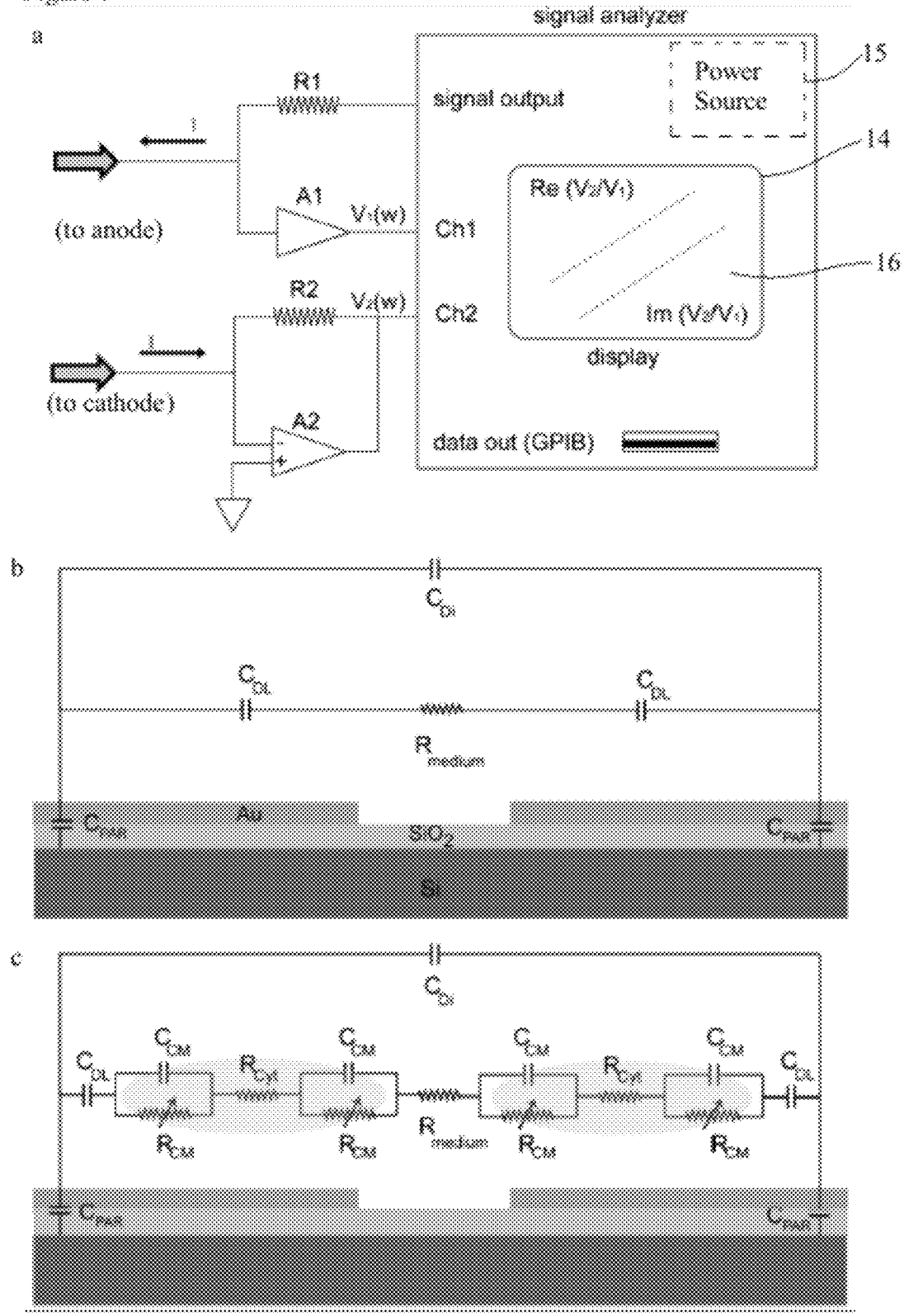
FIG. 1(A) depicts a schematic of the impedance spectroscopy measurement setup.
FIG. 1(B) depicts a simplified equivalent circuit of the microelectrode array/electrolyte interface before bacterial binding.
FIG. 1(C) depicts a simplified equivalent circuit of the microelectrode array/electrolyte interface after bacterial binding.

As used herein, the phrase "low frequency" refers to a frequency below 1 MHz.

As used herein, the phrase "high frequency" refers to a frequency above 20 MHz.

As used herein, the phrase "electrical conductivity" refers to the electrical resistance and/or impedance of a material.

As used herein, the initials "PCR" refers to polymerase chain reaction.

As used herein, the acronym "ELISA" refers to enzyme-linked immunoassay.

As used herein, the initials "AMP" refers to antimicrobial peptides.

As used herein, the acronym "NEMS" refers to nanomechanical cantilever sensing.

As used herein, the acronym "SERS" refers to surface-enhanced Raman spectroscopy.

As used herein, the initials "LPS" refers to lipopolysaccharide.

As used herein, the acronym "SNAP" refers to superlattice nanowire pattern transfer.

As used herein, the initials "NW" refer to nanowires. Similarly, as used herein, the initials "SiNW" refer to silicon nanowires.

As used herein, the initials "FMOC" refer to fluorenyl-meth-oxycarbonyl.

As used herein, the initials "O-HP" refer to Odorranin-HP, an antimicrobial peptide isolated from the skin of the frog species *Odorrana grahami*.

As used herein, the initials "IMA" refer to interdigitated microelectrode array.

As used herein, the initials "PECVD" refer to plasma enhanced chemical vapor deposition.

Current methods for detecting pathogenic bacteria include enzyme-linked immunoassay (ELISA), and polymerase chain reaction (PCR). In the former case, the assays exploit antibodies as molecular recognition elements due to their highly specific targeting of antigenic sites. However, antibodies lack the stability needed to detect pathogenic species under harsh environments, reducing the shelf life of antibody functionalized sensors. The high specificity of antibody-antigen interactions also requires a one-to-one pairing of antibody-based sensors for each target to be detected. Nucleic acid probe-based techniques such as PCR can reach single-cell detection limits, yet require the extraction of nucleic acids and are limited in portability.

By contrast, the ease of synthesis and intrinsic stability of antimicrobial peptides (AMPs) render them particularly good subject matters for use as molecular recognition elements in bioelectronic sensing platforms. Anti-microbial peptides are a class of biomolecules, which appear in multiple niches in nature including the skin of higher organisms and the extracellular milieu of bacteria as the primary line of defense against bacteria and fungi. It is of particular note that AMPs are much more stable than typical globular proteins explaining why they can be continually exposed to the environment and are exceptionally efficient at fending off bacterial infection. Indeed, some cationic antimicrobial peptides have shown activity toward pathogenic bacteria under harsh environmental conditions such as thermal (boiling/autoclaving) and chemical denaturants. The replacement of current antibody based affinity probes with more stable and durable AMPs in biological sensors may thus help to increase the shelf-life of current diagnostic platforms. A final major advantage of AMPs as recognition elements stems from their semi-selective binding nature to the target cells, affording each peptide the ability to bind to multiple pathogenic cells.

The durability and ruggedness of AMPs has led others to utilize AMPs as an enhancement to various devices to provide antimicrobial features. U.S. Patent Application Publication Nos. 2005/0065072 to Keeler et al., 2004/0126409 to Wilcox et al., and 2007/254006 to Loose et al. and European patent No. EP 0 990 924 to Wilcox et al. (all of which are hereby incorporated by reference in their entireties) describe various methods of attaching antimicrobial peptides to a variety of substrates for the purpose of producing a device with antimicrobial properties.

A number of methods have been successful at detecting bacteria including nanomechanical cantilever sensing (NEMS), surface-enhanced Raman spectroscopy (SERS), and quartz crystal microbalance based sensors. Similarly, recent attempts have utilized AMPs as biorecognition elements in fluorescent-based microbial detection with achievable detection limits of $5 \times 10^4$ cells/mL. There have been previous attempts to create a biosensor that utilizes AMPs to detect bacteria. Notably, Kulagina et al. report the use of AMPs in a biosensor in U.S. Publication 2006/0281074. However, it is worth particularly pointing out that Kulagina et al. used a florescent-based detection method which lacks the portability and near instantaneous results that are desirable in a biosensor. The biosensor of Kulagina et al. also does not permit real time testing of sample in a flow-through system, another desirable feature.

Detectors with real-time capabilities have been shown by others. However, these detectors lack the sensitivity and versatility of the biosensor described herein. For instance, low field, low frequency, dielectric spectroscopy, as will be described further herein, has previously been used to analyze biologic material, see Prodan et al. (2004) J. Applied Physics 95(7): 3754-3756, hereby incorporated by reference in its entirety. However, Prodan et al. lack sensitivity for a particular target. Prodan et al. do not use a biologic binding molecule to detect cells merely the difference in impedance of different frequencies of current through a cell suspension to determine cell concentration. It is also worth noting that the power source used in the study by Prodan et al. is hard wired into the detector. The detector of Prodan et al. lacks the specificity, portability and variability that would be desirable in a biosensor.

The development of an "all-in-one" solution which combines a high degree of portability, robustness, sensitivity, and selectivity toward pathogenic strains remains challenging. There exists a need for a highly portable biosensor device of pathogenic strains that is robust, sensitive and selective. It is also highly desirable if the biosensor could be configured to operate on a variety of power sources, including DC power, AC power and battery-free power. It further desirable if the biosensor was scalable, so that it could function at laboratory size, handheld size and at nanometer size.

Biosensor

A label-free electronic biosensor based on the hybridization of the antimicrobial peptide with an electrode array for the sensitive and selective detection of antimicrobial peptide targets via impedance spectroscopy is disclosed. Specifically demonstrated is a label-free electronic biosensor based on the hybridization of the antimicrobial peptide magainin I with interdigitated microelectrode arrays for the sensitive and selective detection pathogenic bacteria via impedance spectroscopy. Furthermore, it is contemplated that the combination of compact, naturally bioselective AMPs with microcapacitive sensors represents a highly robust and portable platform for fundamental development of AMP-bacteria interactions, and for portable infectious disease threat agent signaling. It is demonstrated that a bioresorbable sensor for highly sensitive and selective detection of biological analytes is possible through the synergistic integration of the smart properties of selectivity in biological recognition possessed by naturally occurring antimicrobial peptides with the high sensitivity of two dimensional graphene nanomaterial transducers on a biocompatible silk fibroin substrate.

The biosensor's sensitivity is especially suited to detection of infectious agents. One aspect that makes the biosensor especially suited to detect infectious agents is its capability to function in virtually any location. It is demonstrated that some embodiments of the biosensor are suitable for field use, for instance in a reservoir, where infectious agents might enter a population's water supply. It is further demonstrated that some embodiments are suitable for use at the point of infection in vivo. It is demonstrated that certain embodiments of the biosensor can be implanted on and used on the surface of a tooth. It is contemplated that the biosensor can be used on nearly any biological surface it can be brought in contact with including, but not limited to tooth, bone, skin, tissue, hair, nail, cornea, gum, tongue, palate, brain, heart, lung, membrane, leaf, root, bark, fur, feather, chiton and scale. It is further contemplated the various embodiments of the biosensor allow the biosensor to be used in nearly any environment, including but not limited to: in soil, in water, airborne, and in vivo. For instance, it is contemplated that nanoscale embodiments of the biosensor could be injected subcutaneously or intravenously for use inside a human or other species. It is further contemplated that the biosensor could be embedded on a substrate and swallowed like a pill as another use in vivo.

Another aspect that makes the biosensor especially suited to detect infectious agents is its high sensitivity. It is demonstrated that the biosensor matches the sensitivity of PCR, in that it can detect levels as low as a single infectious unit (see Example 10). Yet, unlike current or imagined applications of PCR, the biosensor can provide this high degree of sensitivity in real time and, as stated above, any location. This ability allows the biosensor to be an effective tool against highly virulent species or strains.

Every pathogen and strain of pathogen can be described in terms of its minimum infectious dose (MID) to cause disease in a particular species, or subclass within a species. Some pathogens have a large MID for a particular species, i.e., a dose of a large number of those pathogens is required for the clinical observation of disease. For instance, in Rhesus monkeys as many as $10^5$ infectious units of *H. Pylori* are required for the onset of disease (Solnick et al. (2001) Determination of the Infectious Dose of *Helicobacter pylori* during Primary and Secondary Infection in Rhesus Monkeys (*Macaca mulatta*) Infection and Immunity, 69 (11): 6887-6892 DOI:

10.1128/IAI.69.11.6887-6892.2001, hereby incorporated by reference in its entirety). For other infectious agents in other species the number of units required to cause disease is much less. Highly virulent infectious agents have a small MID against the most susceptible of hosts. For instance, as little as 10 viable cells of *Shigella flexneri, Shigella sonnei* or *Shigella dysenteriae* are needed to cause bacillary dysentery in humans (Schaad U. B. (1983) Which Number of Infecting Bacteria is of Clinical Relevance? Infection 11, Suppl. 2, S87-S89, hereby incorporated by reference in its entirety). Therefore, it is especially necessary for biosensor to be able to detect as little as 10 or fewer infectious agents to be effective as an alert to the most virulent of agents.

Transduction of Binding Event

Among the various label-free signal transduction platforms that are known, impedance spectroscopy is most ideal due to its simple instrumentation, ease of device assembly, and adaptability to multiplexed lab-on-a-chip applications. A microcapacitive sensor detects impedance changes in the dielectric properties of an electrode surface upon analyte binding, where the variation in the impedance is directly proportional to the activity of analyte binding.

FIGS. 1A-1C show schematics of a measurement setup. In this example, an AC voltage applied to the electrodes produces both conduction and displacement current through the sample. The real and imaginary parts of the transfer function $V2(w)/V1(w)$ are proportional to the conductivity and the dielectric constant, respectively. The output of the signal analyzer is applied to one of the capacitive electrodes through R1. The other electrode of the capacitive sensor is connected to the negative input of the amplifier A2, which holds the electrode at ground potential. As a result, the current I that flows through the sensor produces a voltage V2 which is equivalent to the product of I and the sample impedance Z. The value of voltage drop V1 is equal to the product of I and R2. Therefore, the transfer function of the system is given by:

$$\frac{V_2(\omega)}{V_1(\omega)} = \frac{Z}{R_2}$$

Where Z is the overall impedance of the sensing system. The purpose of R1 is to provide an upper limit for the current I as the impedance Z becomes smaller at higher frequencies. The unity gain amplifier A1 provides buffering so that the input impedance of Channel 2 does not affect the voltage drop across the sample.

A high density interdigitated microelectrode array can be used for the detection of bacterial cells. The exposure of the magainin functionalized sensor to bacterial cells results in the binding on the cells on the electrode surface. Bacterial binding of bacterial cells causes change in the impedance measured across the electrodes. FIG. 1A shows an equivalent circuit of the microelectrode solution interface before the binding bacterial cells. A display unit 14 is coupled to the biosensor anode and cathode. The display unit includes a readout 16 configured to indicate the conductivity, e.g., resistance and/or impedance, of the biosensor. It should be understood that circuits disclosed herein may also include a power source as generally shown by block 15. $C_{DL}$ represents the capacitance due to the electrical double layer between the electrode and the buffer solution, $C_{Di}$ represents the dielectric capacitance, and $R_{Buffer}$ the bulk resistance of the buffer solution. A parasitic capacitance from the oxide layer between silicon and gold is shown as $C_{PAR}$. FIG. 1B shows a simplified circuit diagram of the system after bacterial binding to the AMP functionalized electrodes. The modification in the interface impedance due to the bacterial impedance consists mainly of the capacitance of the cell membrane $C_{CM}$, the resistance of the membrane $R_{CM}$, and the resistance of the cytoplasm $R_{Cyt}$, as shown. The represented model has two parallel branches, a dielectric capacitance branch and an impedance branch. At high frequencies, the total impedance of the system Z will be dominated by the dielectric capacitance of the medium, and the contributions from the electrical double layer capacitance and the bulk medium resistance will be minimized. At lower frequencies (<1 MHz), current does not flow through the dielectric capacitance branch, and the bacterial cells bound to the electrodes add different impedance components in series to the impedance branch.

Sensitivity Measurements

As a test case for the demonstration of an AMP-based label-free, electronic biosensor, the targeting of microbial cells by magainin I was conducted using impedance spectroscopy. FIG. 2 schematically outlines the sensing platform. AMPs are first immobilized on microfabricated interdigitated gold electrodes, anode 10 and cathode 12 (FIG. 2A). Magainin I was acquired with an additional cysteine residue at the C-terminus (FIG. 2B), allowing for facile and site specific covalent attachment to the gold electrodes. Next, heat-killed bacterial cells were injected and incubated with the AMP-modified electrodes. If the bacteria are recognized by the AMPs, binding will occur (FIG. 2C), leading to dielectric property changes which can be monitored via a spectrum analyzer. The impedance was measured over a frequency range of 10 Hz to 100 kHz. FIG. 2D shows an optical micrograph of the device, which is made using standard microfabrication techniques.

Figure 3A:
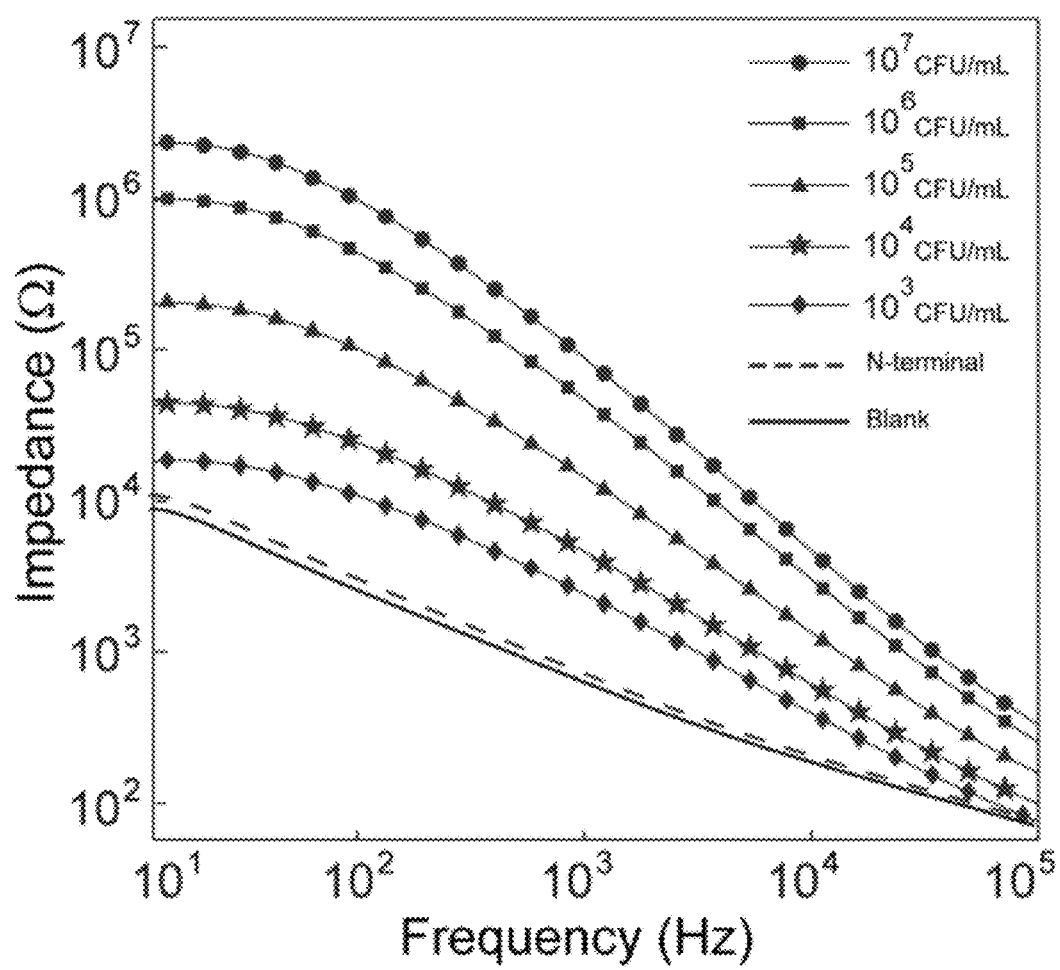
FIG. 3(A) depicts a line graph of the sensitivity of the AMP electronic biosensor of impedance spectra of various concentrations of $E.\ coli$ O157:H7 cells (lines with geometric shapes), of a nonlabeled sensor (solid line), and of a sensor with an N-terminal immobilized AMP (dashed line)
Figure 3B:
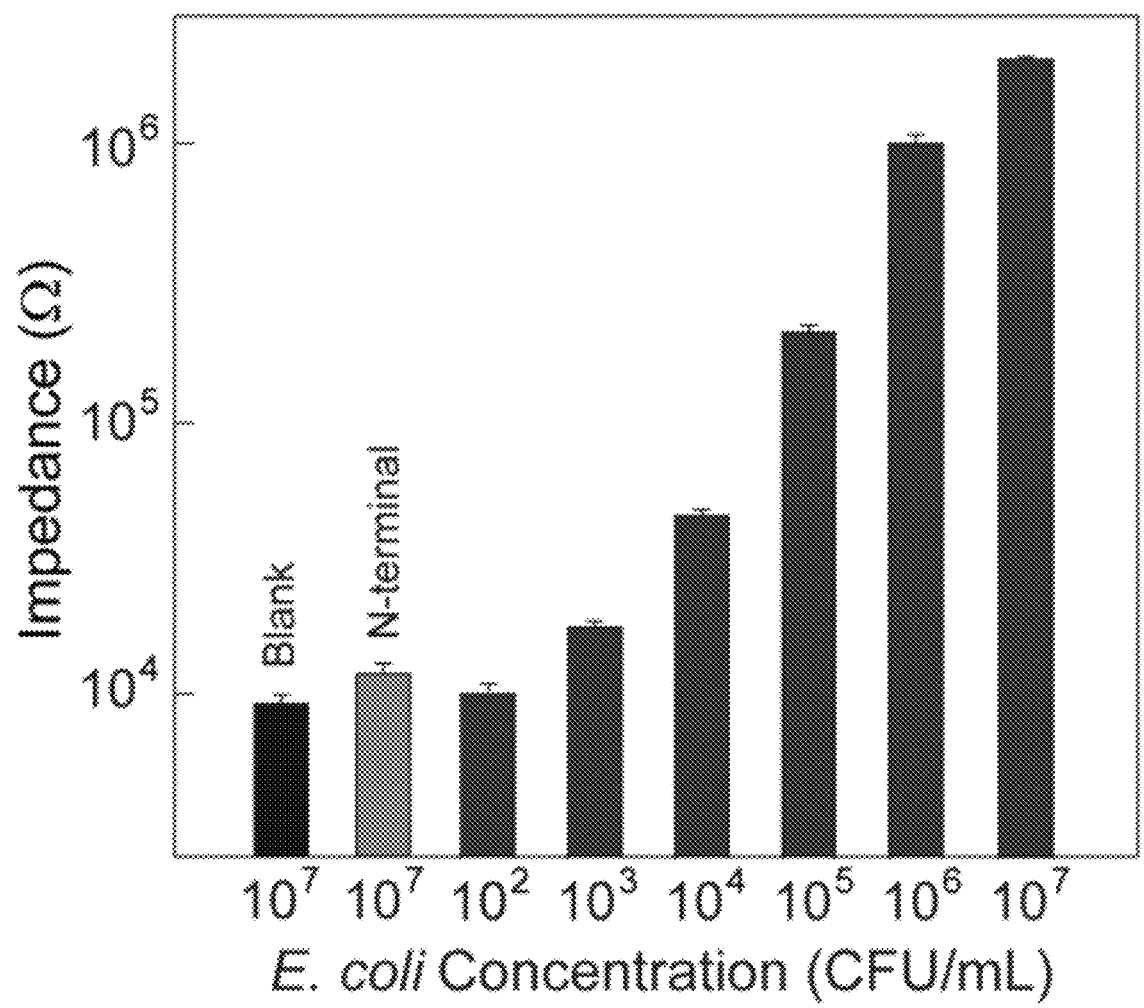
FIG. 3(B) depicts a bar graph of the impedance spectra of various concentrations of $E.\ coli$ with the AMP sensor at 10 Hz, error bars show standard deviation (N=3)
Figure 4:
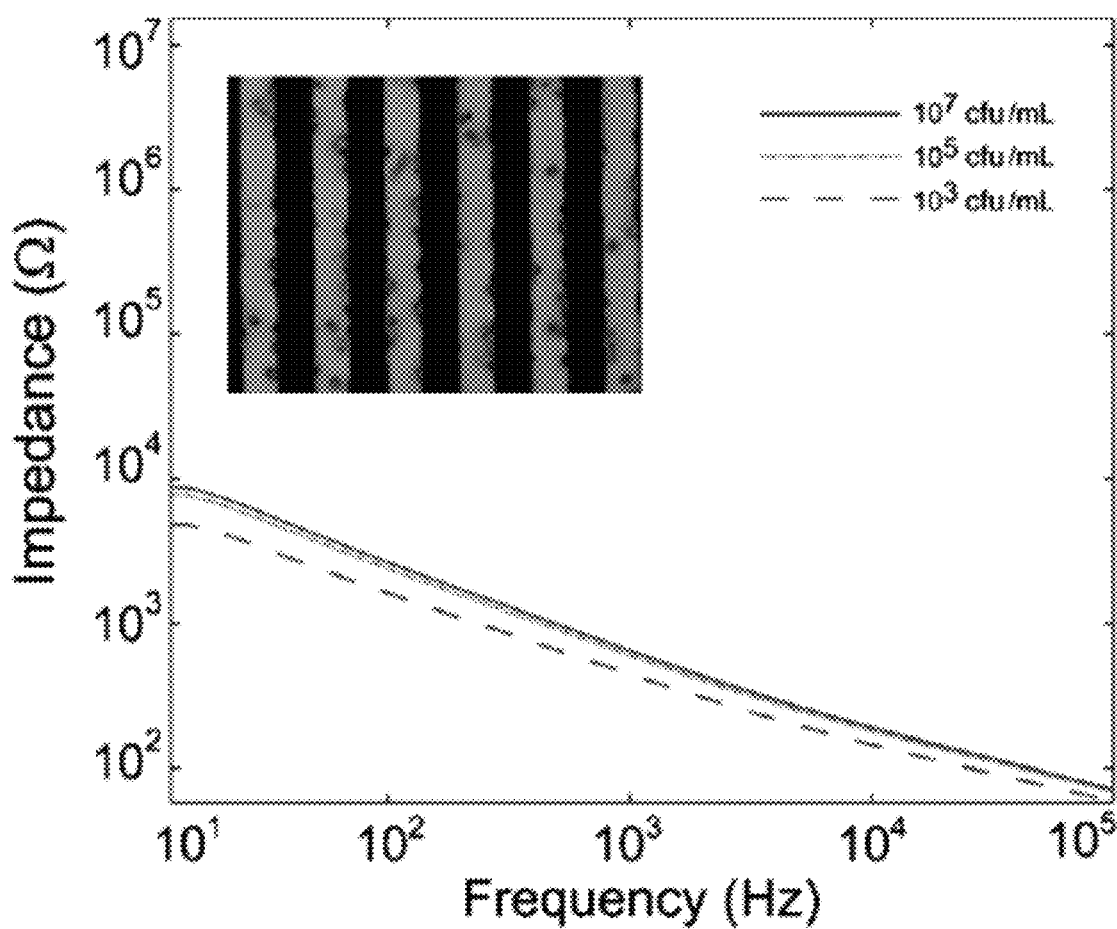
FIG. 4 depicts a line graph of the impedance spectra of various concentrations of $E.\ coli$ O157:H7 cells after exposure to a nonlabeled "blank" sensor, the inset shows the optical micro-graph of the bare sensor after exposure to $E.\ coli$ cells of concentration $10^7$ cfu/mL.

Sensitivity of microbial detection is a key determinant for utility of the biosensor. To this end, the sensitivity of the magainin-functionalized microelectrode array in detecting bacterial cells was determined using impedance spectroscopy. FIG. 3 shows the results of measurements performed after incubation of the immobilized AMPs with pathogenic *E. coli* O157:H7 cells in concentrations ranging from $10^3$ to $10^7$ CFU/mL. A "blank" device with no immobilized AMPs was also tested for comparison. FIG. 3A shows that at low frequencies, the different concentrations of bacterial cells have the effect of increasing the impedance in proportion to the number of cells present in the sample for concentrations greater than $10^2$ CFU/mL. As the frequency increases, the contribution to the impedance from the bacterial cells decreases, leaving only the dielectric relaxation of small dipoles including water molecules in the buffer solution to affect the measured impedance. FIG. 3B depicts the impedance change at the fixed frequency of 10 Hz. The variation in the impedance is directly proportional to the number of bacterial cells bound to the immobilized AMPs and manifested in a logarithmic increase with respect to serially diluted bacterial concentrations. Significantly, the detection limit of response of the hybrid AMP-microelectrode device to *E. coli* is found to be $10^3$ CFU/mL (1 bacteria/µL), as the dielectric polarization of the bacterial cells bound to the surface of the electrodes begins to have an effect on the base impedance of the capacitive electrodes at this concentration (see FIG. 4). This sensitivity limit is clinically relevant and compares favorably to AMP based fluorescent assays [$5 \times 10^4$ CFU/mL] and to antibody-based impedance sensors. This lowest limit of detection appears to be limited by the presence of impedance due to the electrical double layer resulting from the electrode polarization effect at low frequencies.

To gain further insight into the sensitivity of the magainin I AMP toward *E. coli*, AMPs were immobilized "upsidedown" via incorporation of a cysteine residue at the N-terminus. The binding affinities of magainin I immobilized via cysteine residues at the C-terminus and N-terminus were compared and co-plotted in FIGS. 3A and 3B. Considerably reduced binding activity was observed for magainin immobilized via the N-terminus compared to C-terminal immobilization.

Without being bound by speculation, it is thought this reduction in the binding affinity is likely due to the diminished exposure of the target bacteria to the amine-containing residues near the N-terminus. This observation supports the hypothesis that the initial interaction of α-helical AMPs with the membranes of the target bacteria occurs via electrostatic attraction of positively charged amino acids on the AMP with negatively charged phospholipids in the bacterial membrane. Indeed, it has been previously shown that amino acid omissions in the N-terminal region of magainin result in the complete loss of antimicrobial activity, whereas analogs with omissions in the C-terminal region exhibited equal or increased activity.

Figure 5:
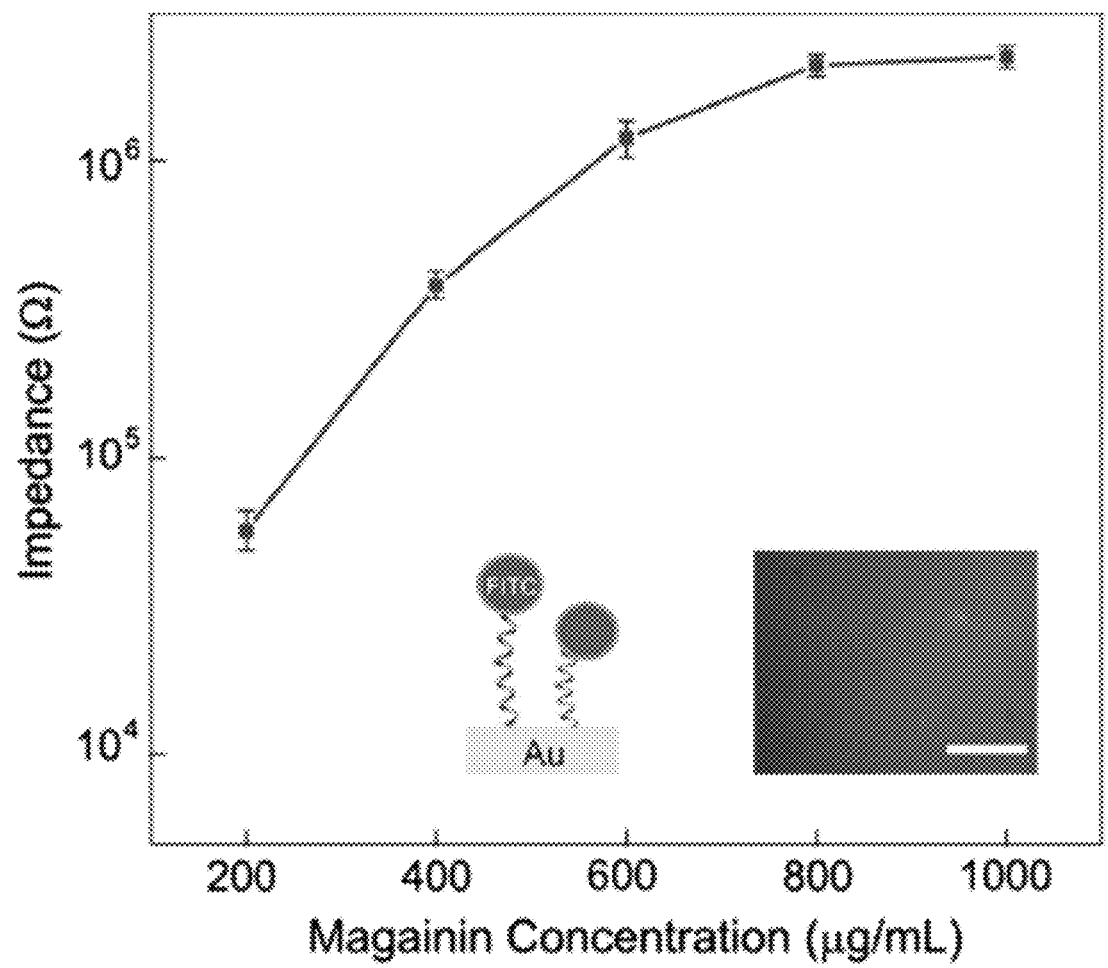
FIG. 5 depicts a line graph of the effect of the surface density of immobilized magainin I on the binding of bacterial cells, error bars show standard deviation, (N=3); the left inset of FIG. 5 depicts an illustration antimicrobial peptide (Magainin I) immobilized on to gold substrate; the right inset of FIG. 5 depicts a fluorescent image of antimicrobial peptide (Magainin I) immobilized on to gold substrate after labeling with FITC dye.

Finally, the effect of varying the surface density of the immobilized AMPs on the detection of bacterial cells was investigated (see FIG. 5). The response of the biosensor towards target cells was found to increase monotonically with increasing concentration of immobilized magainin.

In an effort to determine the optimal performance of the biosensor, the value of varying the surface density of the immobilized AMPs on the detection of bacterial cells was explored. Different concentrations of C-terminal cysteine labeled magainin I were immobilized on the electrode surface. The impedance response resulting from binding of pathogenic $E.\ coli$ O157:H7 cells ($10^7$ CFU/mL) to different densities of immobilized AMPs were recorded. The response of the sensor at 10 Hz is plotted in FIG. 5. The immobilized peptide film was also analyzed via fluorescent microscopy by labeling the peptides with fluorescein isothiocyanate (FITC). The ability to capture the target bacteria was found to be strongly dependent on the immobilization density of the magainin on the sensor surface. This supports the hypothesis that the initial interaction between the cationic AMPs and the target species occurs through electrostatic interaction. This also suggests that the minimization of diffusion and steric hindrance, which usually affect the binding kinetics, do not play a significant role in the immobilized AMP-bacteria interactions.

Selectivity Measurements

Figure 7A:
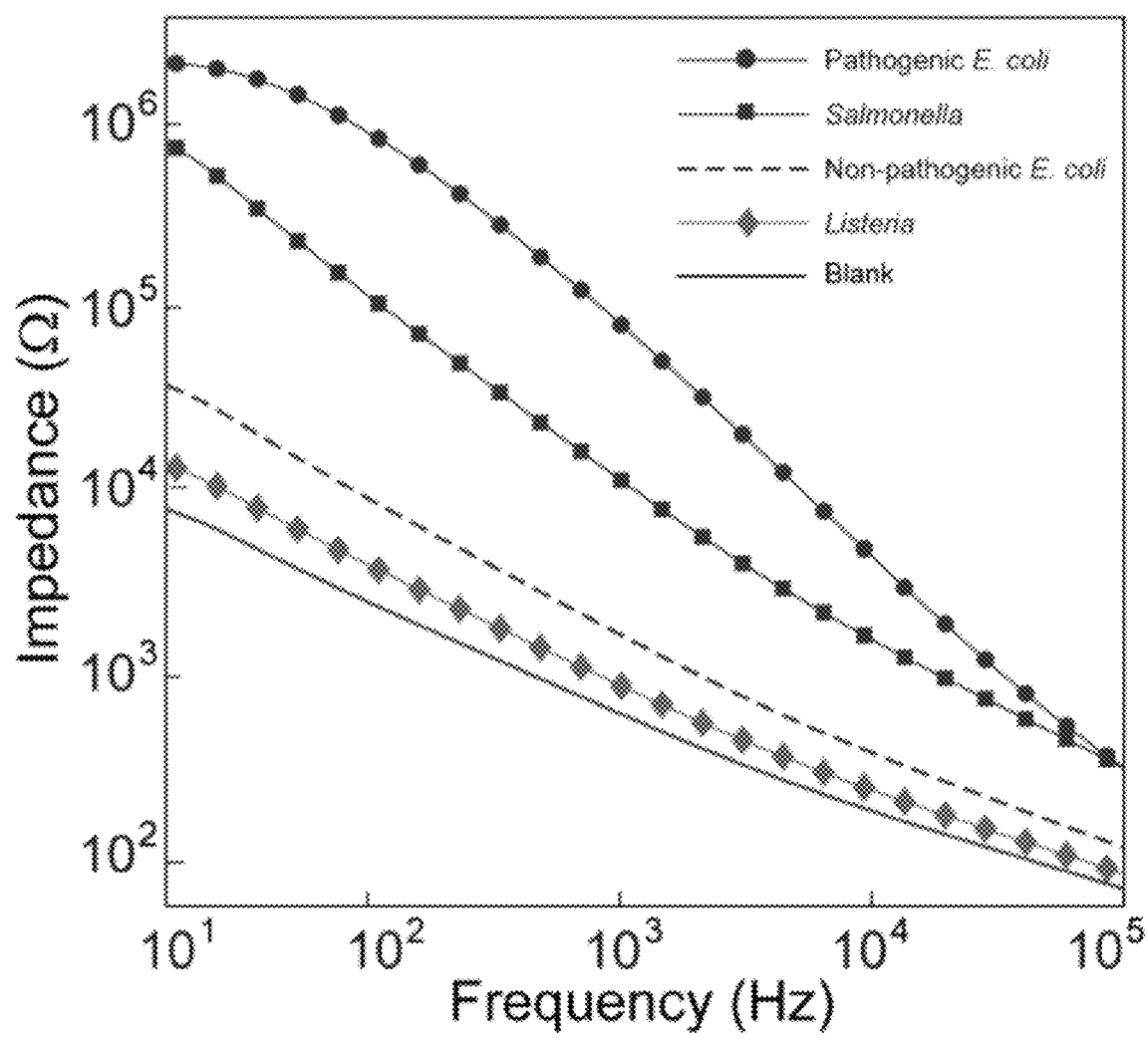
FIG. 7(A) depicts a line graph of the impedance spectra of the AMP-functionalized microelectrode array after interaction with various bacterial samples ($10^7$ cfu/mL)
Figure 7B:
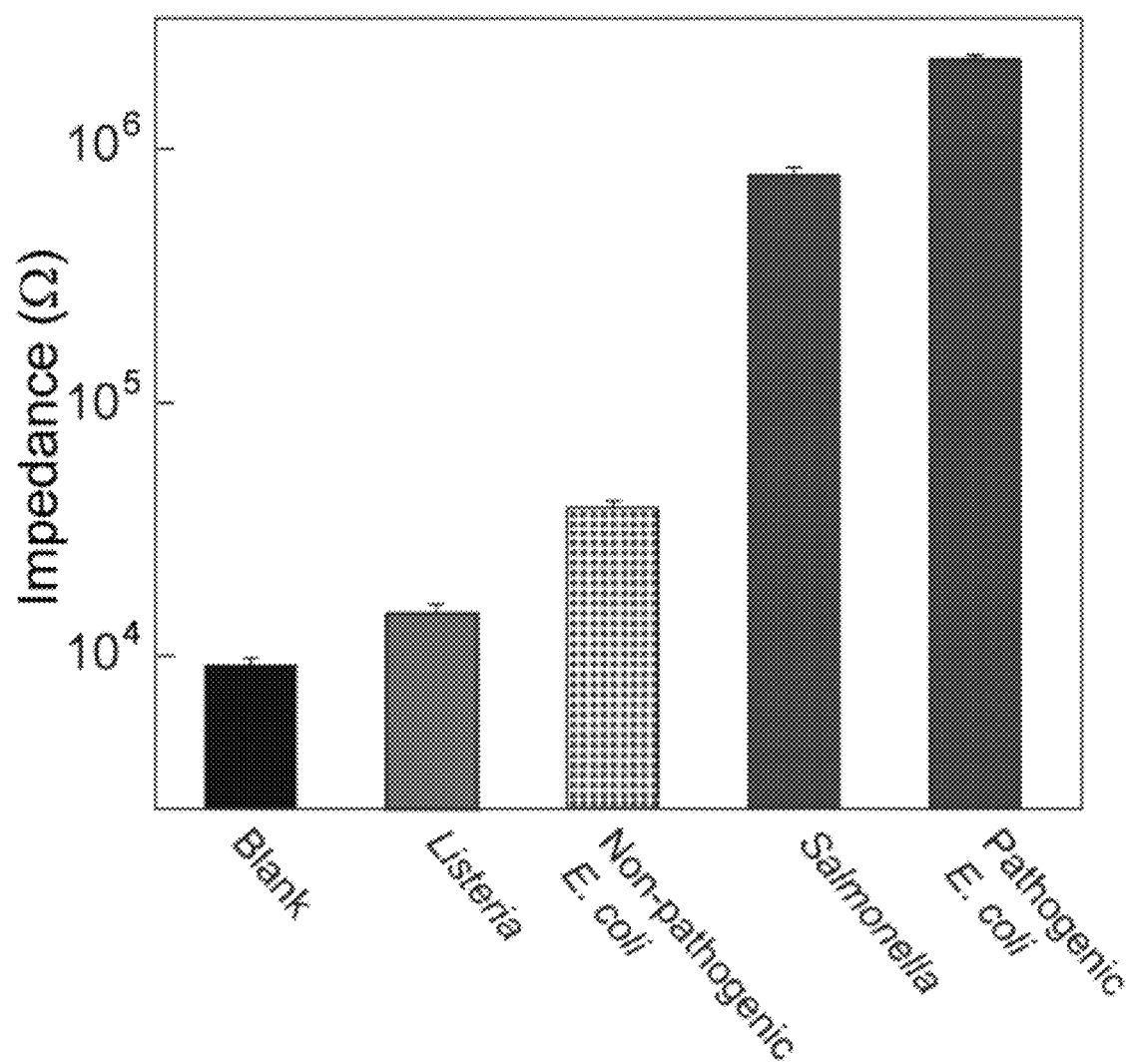
FIG. 7(B) depicts a bar graph of the impedance changes associated with various bacterial species at 10 Hz, error bars show standard deviation (N=3)

As a next step, the selectivity of the AMP-functionalized biosensors toward various bacterial species was determined. Specifically, the binding behavior of AMPs was probed toward: 1) Gram-negative pathogenic $E.\ coli$ O157:H7, 2) the non-pathogenic $E.\ coli$ strain ATCC 35218, 3) Gram-negative pathogenic $Salmonella\ typhimurium$, and $Listeria\ monocytogenes$, a Gram-positive pathogen. Collectively, these studies elucidate the matrix of selectivity as it depends on Gram-negative vs. Gram-positive species, and pathogenic vs. non-pathogenic strains. The selectivity was first investigated using fluorescent microscopy methods, by staining bacterial cells and optically mapping their binding density to gold films hybridized with AMPs. FIG. 6 shows the discriminative binding pattern of immobilized magainin I to various bacterial cells (all $10^7$ CFU/mL) stained with propidium iodide (PI) nucleic acid stain, as well as the surface density of the bound bacterial cells. Likewise, FIG. 7A plots the electrical response of the AMP-biosensor against these various species as a function of the interrogating frequency, and FIG. 7B plots the response at 10 Hz.

As a proof of principle, inspection of the fluorescent images and surface density plots agree qualitatively with the response of the AMP electrical biosensor and reveal the following performance characteristics. First, magainin I exhibits clear preferential binding toward the pathogenic, Gram-negative species $E.\ coli$ and $Salmonella$, relative to the Gram-positive species $Listeria$, with a two order of magnitude impedance difference at 10 Hz (FIG. 7B). This selectivity was particularly enhanced for pathogenic $E.\ coli$, which showed slightly larger response relative to $Salmonella$. Next, inter-bacteria strain differentiation between pathogenic and non-pathogenic bacteria is demonstrated by the ability of the sensor to selectively detect pathogenic $E.\ coli$ relative to the non-pathogenic strain, again with a nearly two order of magnitude impedance difference at 10 Hz. Finally, the response of the sensor to all microbial species was larger than the response of the "blank" biosensor which was not functionalized with AMP.

The observed specificity differences provide support for a balance between electrostatic and hydrophobic interactions that is the underlying hypothesis of the mechanism of binding to bacterial cells by AMPs. In the case of magainin I, the difference in the membrane structures of Gram-negative vs. Gram-positive bacteria accounts for the differential selectivity. Gram-negative bacteria possess an outer membrane with negatively charged lipopolysaccharide (LPS)—the first site of encounter for AMPs—and a thin peptidoglycan layer. In contrast, Gram-positive bacteria lack the LPS containing outer membrane and instead possess a thick peptidoglycan layer and teichoic acids. Further, although both pathogenic and non-pathogenic $E.\ coli$ cell walls contain LPS, the LPS of pathogenic strain includes O-antigens, which are hydrophilic branched sugar side chains. These O-antigens form the outermost portion of the polysaccharide chain and are thought to enhance electrostatic and hydrogen bonding. This ability of magainin I to selectively prefer Gram-negative species, and pathogenic versus non-pathogenic strains of $E.\ coli$, agrees with several other bacteria adhesion studies. Therefore, it is expected that AMPs will perform as part of the biosensor as the AMPs are observed to function in vivo.

Real-Time Detection

Figure 8:
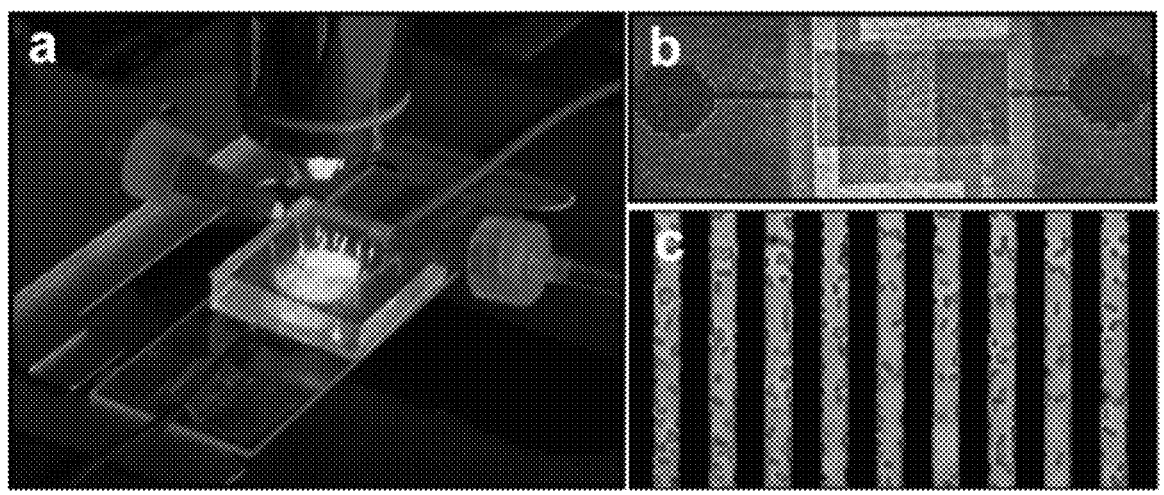
FIG. 8(A) shows a photograph of the microfluidic flow cell during real-time binding of bacteria to AMP biosensors.
FIG. 8(B) shows an optical micrograph of the microfluidic channel with an embedded interdigitated microelectrode array chip.
FIG. 8(C) shows an optical image of the embedded microelectrode array after exposure to $10^7$ cfu/mL bacterial cells for 30 min.
FIG. 8(D) depicts a graph of real-time monitoring of the interaction of the AMP-functionalized sensor (and an unlabeled control chip) with various concentrations of $E.\ coli$ cells.
Figure 8D:
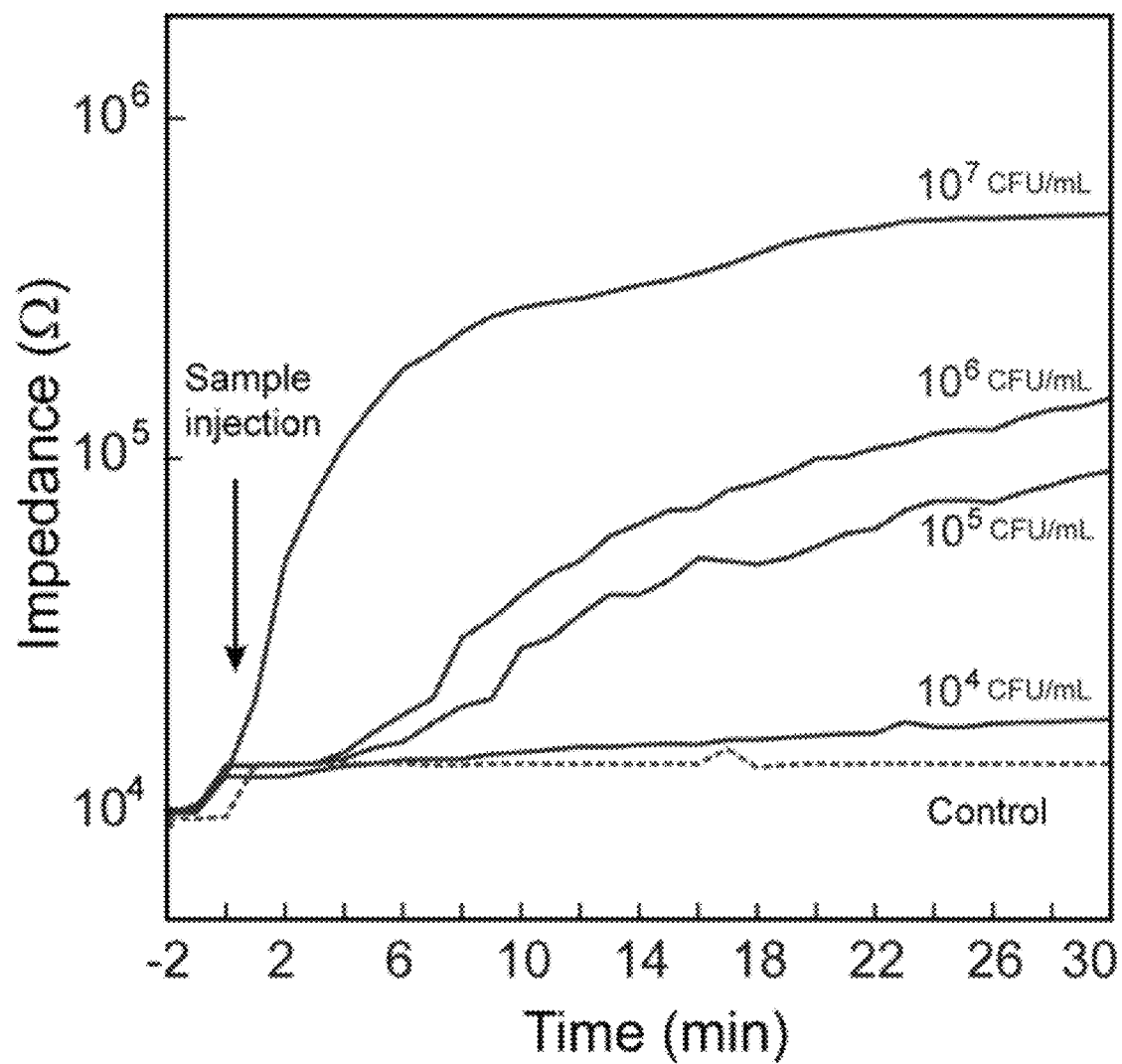

To simulate the use of the AMP microelectrodes in everyday applications, such as direct water sampling, the biosensor response tested to perform in real time, as shown in FIG. 8. First, a microfluidic cell was bonded to the interdigitated biosensor chip (FIG. 8A), such that the electrodes were perpendicular to the direction of the sample flow (FIG. 8B). Next, fluid was injected using a syringe pump connected to the inlet port, and allowed to flow through to the outlet port, at a flow rate of 100 μL/min. The flow cell was first flushed with buffer to establish a baseline. Various dilutions ($10^4$-$10^7$ CFU/mL) of pathogenic $E.\ coli$ cells in PBS were then injected to the channel at a reduced flow rate of 5 μL/min for 30 min. For example, FIG. 8C shows the microelectrode array after exposure to $10^7$ CFU/mL bacterial cells. Simultaneously, the impedance response was continuously monitored during the sample flow-through process (FIG. 8D). Significantly, all samples produced a measurable response relative to the control sample within 5 minutes, with the highest concentration sample yielding a response within 30 seconds; these responses saturated after ca. 20 min. Although these results bode well for the implementation of this sensor in continuous monitoring of flowing water supplies, it should be noted that for the same concentration of bacterial cells, the response of the sensor under flow-through conditions was found to be comparatively lower than the response after static incubation. This difference between detection in flowing and static water sample has also been reported in fluorescent based assays. This difference is attributed to the opposing effects of shear and mixing on the binding kinetics.

In summary, coupling of AMPs with microcapacitive biosensors has resulted in the development of a portable, label-free sensing platform for the detection of infectious agents. The achievable sensitivity approached 1 bacterium/µL—a clinically relevant limit—and the AMPs allowed for sufficient selectivity to distinguish pathogenic and Gram-negative bacteria, while retaining broadband detection capabilities. Finally, real-time sensing results demonstrated the capability of the relatively simple impedance-based transduction architecture to directly detect bacteria, demonstrating an improvement to traditional antibody based immunoassays. These results provide a significant positive improvement on the use of pathogenic sensors to test and monitor bacteria in reservoir water, or for use as biological threat agent detection systems. It is contemplated that this biosensor can be utilized for the detection of bacteria in real water samples.

It is further contemplated that these biosensor configured with AMP peptides coupled to silicon nanowire sensors will produce sensor with significantly enhanced sensitivity and a size of the nanometer scale.

Antimicrobial Peptides

Small, cationic antimicrobial peptides (AMPs) are naturally occurring antibiotics of the innate immune system. AMPs are widely distributed in animals and plants and are among the most ancient host defense factors. Their spectrum of activity may include Gram-positive and Gram-negative bacteria as well as fungi cancer cells, certain viruses and some multicellular animal cells.

The bioactivity of AMPs toward microbial cells is classified into groups according to their secondary structures. Many AMPs adopt amphipathic conformations that spatially cluster hydrophobic from cationic amino acids, thereby targeting the negatively charged head groups of lipids in the bacterial membrane. In contrast, the membranes of plants and animals seclude negative charges to the inner leaflet, and contain cholesterols which reduce AMP activity. By aiming at the very foundation of the bacterial cell membrane, and remaining generically unrecognizable to proteases, AMPs as antibiotics have remained remarkably free of acquired resistance. It is therefore anticipated that AMPs represent a class of biomolecules that will continue to bind to a target cell membranes despite genetic drift and mutation within the population. AMPs can also be expected to bind to targets cell membranes across a wide range of geographic areas wherein there many be variation local of strains and species of target cell membranes.

Among AMPs, linear cationic peptides such as magainins are particularly suited for use with the biosensor because of their small molecular size and intrinsic stability. In particular, the positively charged AMP magainin I (GIGKFLHSAGKF-GKAFVGEIMKS) (SEQ ID NO: 1) binds most selectively to the bacterial cell E. coli O157:H7 as a precursor to bactericidal activity. Magainin I also displays broad spectrum activity toward other Gram-negative bacteria, which comprise the majority of pathogenic infection in humans. Therefore, Magainin I is an ideal test case for demonstrating the capabilities of the biosensor.

However, the biosensor is not limited for use with Magainin I. Virtually any AMP, modified AMP, or AMP binding motif, can be used with the biosensor. The criteria for suitability with the biosensor is (1) a known target to which the candidate AMP selectively binds and (2) the ability to immobilize the AMP, modified AMP, or AMP binding motif, to an electrode without disabling the ability of the peptide to selectively bind its target.

There exists an AMP database with which it is possible to search for known AMPs with desirable characteristics. Currently, the AMP database lists 18 AMPs with known affinity to E. coli. These peptides are shown in Table 1. The database can currently be found that the following internet address: aps.unmc.edu/AP/main.php

TABLE 1

| BD REF ID | Name | Sequence | SEQ ID NO |
|---|---|---|---|
| AP00580 | Nigrocin-2GRb | GLFGKILGVGKKVLCGLSGMC | 2 |
| AP00678 | K9CATH | RLKELITTGGQKIGEKIRRIGQR IKDFFKNLQPREEKS | 3 |
| AP00807 | Enterocin E-760 | NRWYCNSAAGGVGGAAGCVL AGYVGEAKENIAGEVRKGWG MAGGFTHNKACKSFPGSGWA SG | 4 |
| AP00846 | Mundticin KS | KYYGNGVSCNKKGCSVDWGK AIGIIGNNSAANLATGGAAGWK S | 5 |
| AP00964 | Dermaseptin-L1 | GLWSKIKEAAKAAGKAALNAV TGLVNQGDQPS | 6 |
| AP01373 | Human TC-1 | AELRCMCIKTTSGIHPKNIQSLE VIGKGTHCNQVEVIATLKDGRK ICLDPDAPRIKKIVQKKLAGDES | 7 |
| AP01374 | Human TC-2 | NLAKGKEESLDSDLYAELRCM CIKTTSGIHPKNIQSLEVIGKGT HCNQVEVIATLKDGRKICLDPD APRIKKIVQKKLAGDES | 8 |
| AP01380 | TBD-1 | YDLSKNCRLRGGICYIGKCPR RFFRSGSCSRGNVCCLRFG | 9 |
| AP01382 | 2B5B, TEWP | EKKCPGRCTLKCGKHERPTL PYNCGKYICCVPVKVK | 10 |
| AP01402 | Ocellatin-V1 | GVVDILKGAGKDLLAHALSKLSE KV | 11 |
| AP01403 | Ocellatin-V2 | GVLDILKGAGKDLLAHALSKISEK V | 12 |
| AP01404 | Ocellatin-V3 | GVLDILTGAGKDLLAHALSKLSE KV | 13 |
| AP01405 | Leptoglycin | GLLGGLLGPLLGGGGGGGGLL | 14 |
| AP01407 | SgI-29 | HNKQEGRDHDKSKGHFHRVVIH HKGGKAH | 15 |
| AP01578 | Myxinidin | GIHDILKYGKPS | 16 |
| AP01591 | cBD-1 | KCWNLRGSCREKCIKNEKLYIF CTSGKLCCLKPKFQPNMLQR | 17 |
| AP01648 | Pelteobagrin | GKLNLFLSRLEILKLFVGAL | 18 |
| AP01753 | Vejovine | GIWSSIKNLASKAWNSDIGQSL RNKAAGAINKFVADKIGVTPSQA ASMTLDEIVDAMYYD | 19 |

It is contemplated that any antimicrobial peptide can be used with certain embodiments of the biosensor. It is further contemplated that certain embodiments of the invention could use modified antimicrobial peptides, or chimeric peptides containing antimicrobial peptide binding motifs and, combinations thereof.

Fields of Use

Biosensors utilizing electrically coupled antimicrobial peptides can be use any field where detecting a target of a known antimicrobial peptide is desirable. These biosensors can be configured with any known antimicrobial peptide, modified AMP, AMP binding motif or a combination thereof. Therefore, they can be used as a diagnostic or monitoring tool in any situation where the detection and analyzes of an antimicrobial peptide target is desirable. The possible uses of the biosensor include but are not limited to applications such as diagnosis, food and water quality monitoring and microbial contamination monitoring in hospitals. Non-limiting examples include use of the biosensor in a hospital laboratory to screen a patient's bodily fluid for infection by a pathogen; use in the field to test a body of water for the concentration of a class or specific bacteria; and interfacing the sensor with patient's tooth through bioresorption of the temporary substrate to enable wireless monitoring and detection of specific pathogenic microorganisms or disease markers in saliva or breath.

Size

As shown in the above examples of use biosensors utilizing electrically coupled antimicrobial peptides can be tailored to a size for almost any proposed use. For instance, if the end use is in a laboratory it may be desirable to use a biosensor of bench-top size. This embodiment of the biosensor could have an AC power source directly coupled to the circuit coupled to immobilized AMPs. Also, in this embodiment of the sensor the microcapacitive sensor may also be directly coupled to the same circuit as the AMPs. It is also contemplated that some embodiments may have an array of circuits each with particular a class or species of immobilized AMPs electrically coupled to a particular circuit. In this embodiment of the biosensor, a plurality of analytes can be detected and the concentrations thereof determined. These different circuits each with its particular AMP could be situated in different channels so that flow of a sample could be directed to the particular AMP circuit. Alternatively, multiple circuits could be situated on a single silicon chip, or similar substrate, with exposure of the sample to all the circuits on the chip.

If the end use of the biosensor is in the field, it may be desirable to have a handheld size device. Such an embodiment of the biosensor could be a portable device. It is contemplated that a battery, typically a DC power source, could power a handheld embodiment of the biosensor. Similar to the AC powered unit described above, the handheld embodiment could have the microcapacitive sensor electrically coupled to the same circuit as the immobilized AMPs. The held-hand size would still permit a design with multiple circuits of different classes or species of AMPs to be combined in a single device.

If the end use of the biosensor is to be in vivo it is desirable that biosensor be sized on order of micrometers or preferably nanometers.

Recently, it has been shown that many types of organic devices including transistors, sensors, and photovoltaic cells can be fabricated on both natural and synthetic flexible polymers including, but not limited to, poly(ethylene terepthalate), poly(imide), poly(ether sulfone), cellulose, paper, silk, silk fibroin and combinations thereof. These polymers are suitable to act as a substrate for immobilized AMPs. Furthermore, it is contemplated that the immobilized AMPs on these substrates could be electrically coupled into a circuit using nanowires. These nanocircuits electrically coupled to immobilized AMPs could be placed anywhere where it would be desirable to detect the analyte of the immobilized AMP. As non-limiting examples, nano-biosensors could be placed in catheters to test for pathogens, or directly on food to detect for contamination and/or spoilage, or in an experimental animal subject to detect bacteria of research study, or in human patients to detect cancerous or precancerous cells or any other threat to the human body, or in the human bloodstream to detect glucose concentration without bloodletting or on the blade of fans to detect air quality, or alternatively nanoscale embodiments could be airborne to detect or seek out air pollutants. The minute size of nanoscale biosensor combined with the described wireless telemetry system allows an embodiment of the biosensor to be used to detect virtually an analyte anywhere.

The substrates listed above in certain situations can be bioresorbed. Gradual bioresorption of the supporting substrates (for instance silk fibronectin) leaves the ultra-thin sensors intimately in place. The nanometer size scale of the sensor allows it to conform to the curvilinear surfaces biological tissues, teeth or any arbitrary substrate.

Highly sensitive and selective biorecognition can be achieved through integration of naturally occurring antimicrobial peptides based biorecognition moieties with highly sensitive graphene transducers.

Such embodiments could be operated with battery-free wireless mechanisms. Battery free operation can be achieved through the magnetic coupling of a planar coil antenna interfaced with the nanomaterial transducers to a remote reader, also enabling subsequent wireless red-out.

Coupling of Peptides to Nanowires.

Figure 9A:
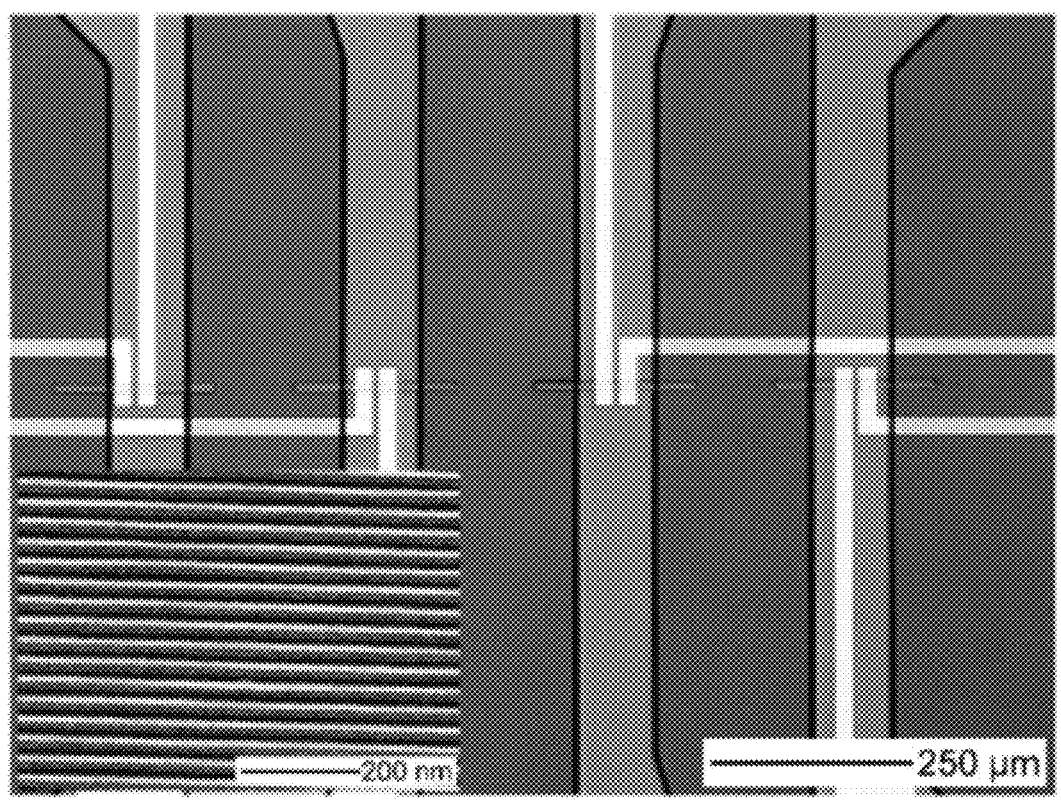
FIG. 9(A) shows the optical image of microfluidic functionalization channels (vertical conduits) intersecting nanowire sensor devices; the nanowire islands (horizontal bars) are electrically contacted by metal leads; the inset depicts a scanning electron micrograph of the nanowire film.
Figure 9B:
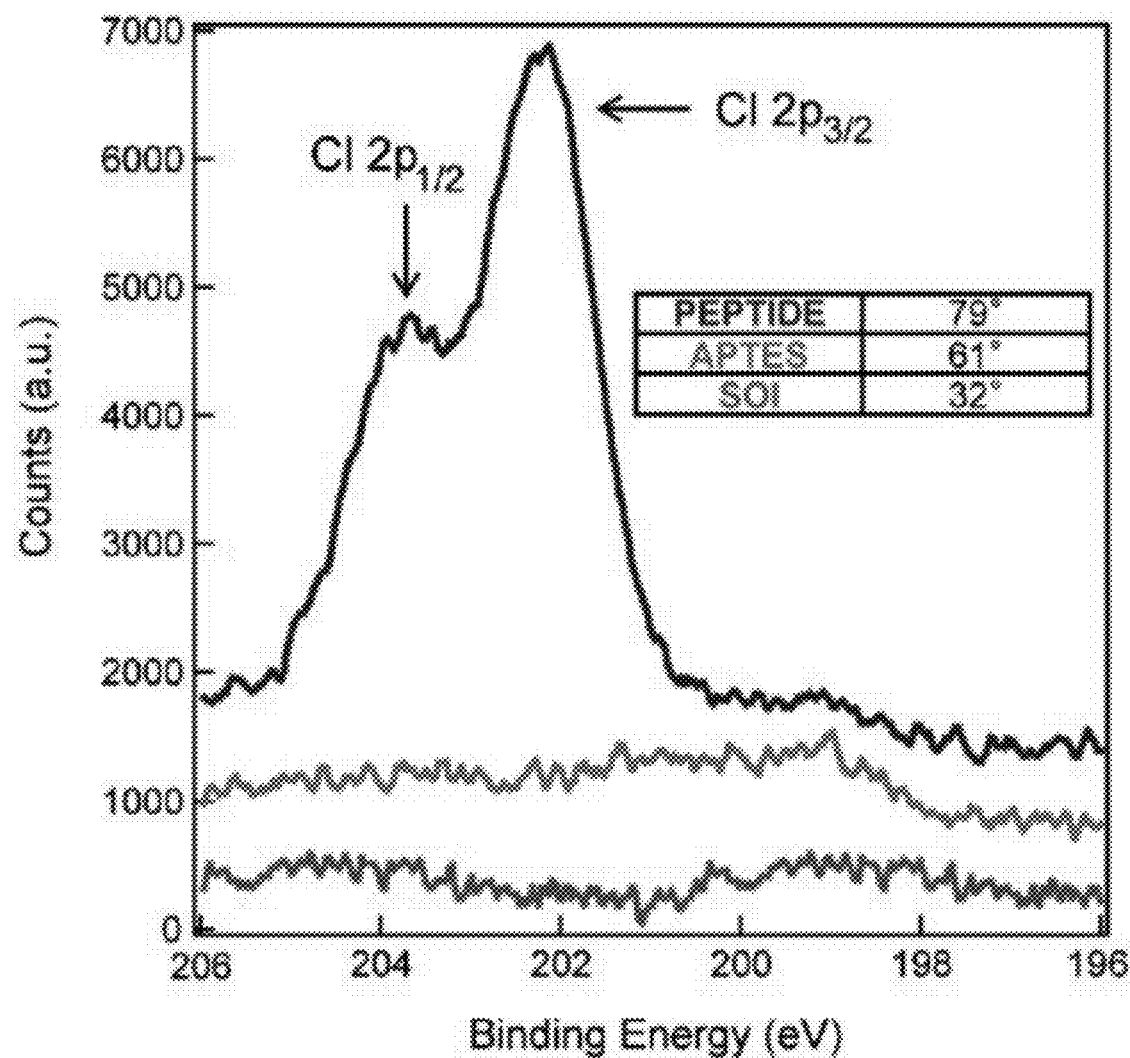
FIG. 9(B) depicts the characterization of the bare silicon-on-insulator (SOI), amine-terminated (APTES), and peptide-coupled surfaces by X-ray photoelectron spectroscopy, the inset depicts water contact angle goniometric measurements of the surfaces.
Figure 10A:
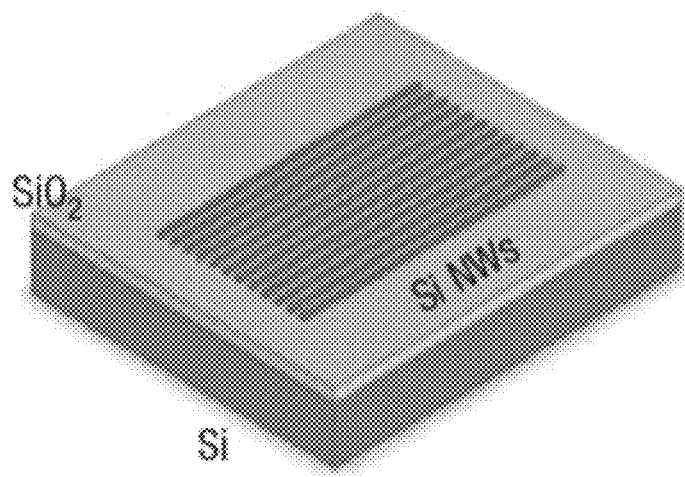
FIG. 10(A) depicts an artistic illustration of first step in which the nanowires are etched into a single-crystal silicon-on-insulator substrate.
Figure 10B:
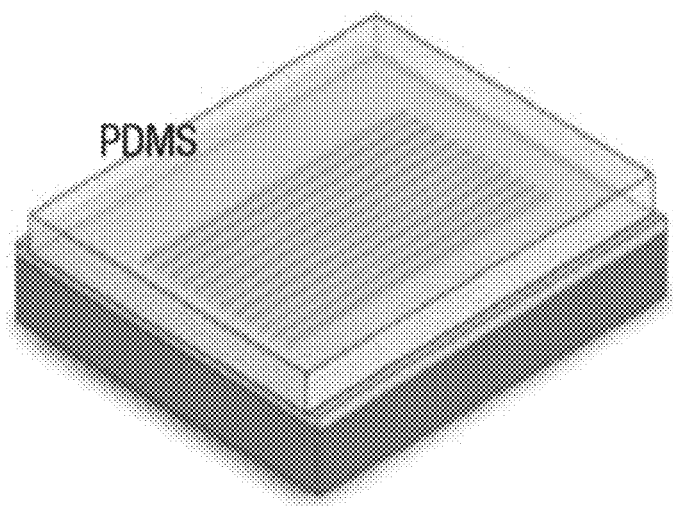
FIG. 10(B) depicts an artistic illustration of the step in which the exposed oxide is etched and a piece of PDMS makes conformal contact with the nanowire surfaces.
Figure 10C:
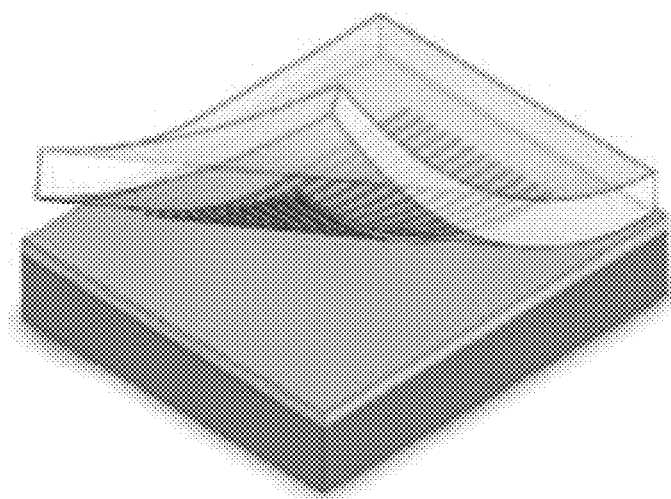
FIG. 10(C) depicts an artistic illustration of the step in which the PDMS with adhered nanowires is peeled back from the host substrate.
Figure 10D:
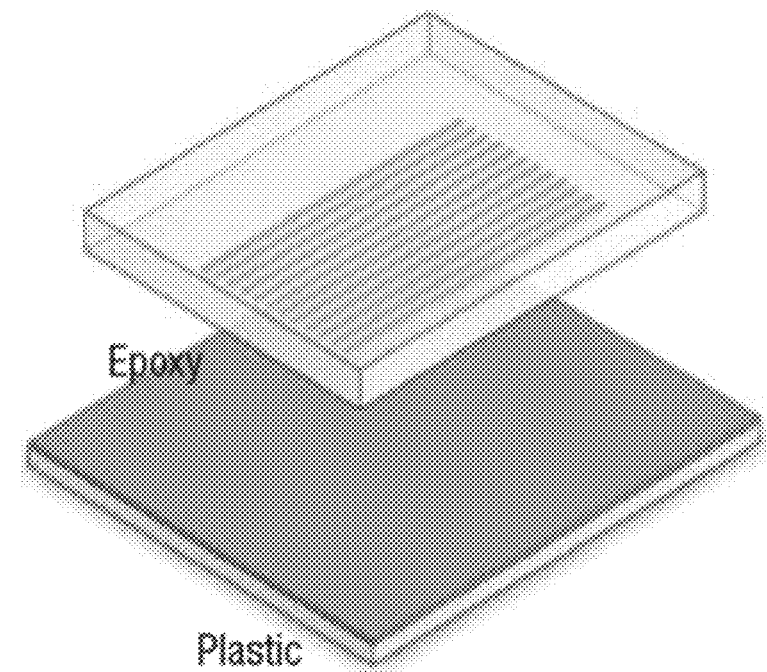
FIG. 10(D) depicts an artistic illustration of the step in which the plastic substrate is spin-cast with epoxy.
Figure 10E:
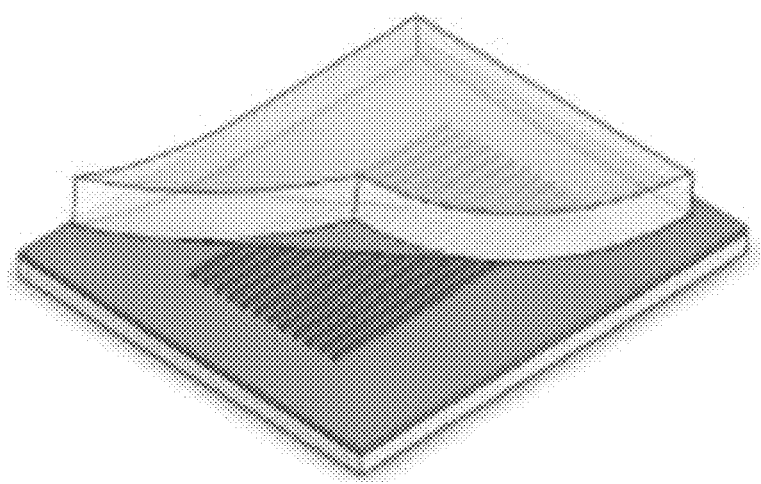
FIG. 10(E) depicts an artistic illustration of the step in which the PDMS makes conformal contact with the plastic, and the epoxy is cured.
Figure 10F:
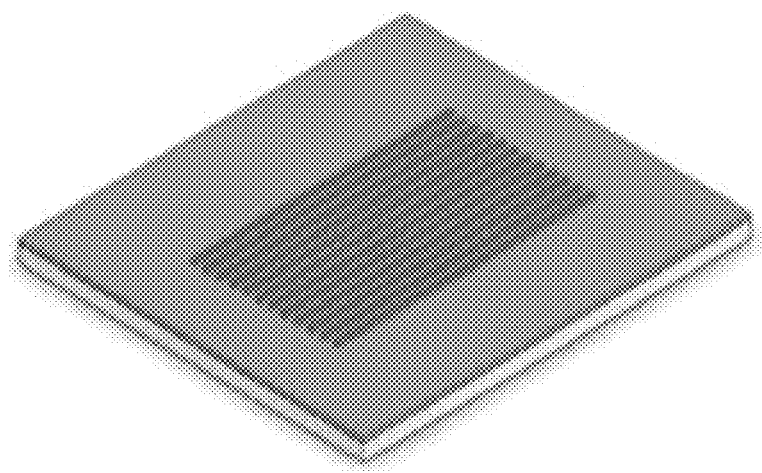
FIG. 10(F) depicts an artistic illustration of final step in which peeling back the PDMS leaves behind the SNAP nanowires in their original orientation, but on plastic.

Silicon nanowires (SiNW) surfaces terminate in intrinsic silica, which has a well-established chemistry, that permits nanowire (NW) surface modification without strongly affecting the semiconducting core. The SiNWs can be fabricated using the superlattice nanowire pattern transfer (SNAP) method, which can be harnessed to produce highly regular arrays of virtually any material that can be obtained as a high quality thin film. A typical NW array may comprise 400 high aspect ratio ($>10^5$), 16 nm wide SiNWs at a pitch of 33 nm, with a p-type doping level of $\sim 10 \times 18/cm^3$. These NWs perform as excellent field-effect transistors on both solid and flexible plastic substrates, with mobilities comparable to that silicon. The SiNWs can be fashioned into sensor devices via conventional microfabrication techniques. A contact metal layer of 1000 Å Ti can be uniformly evaporated across the entire chip and subsequently patterned via photolithography and HF etching to form source/drain finger electrodes across the SNAP wire array. The NW film can be then sectioned into individual sensor elements using photolithography and etching. As an example of sensitivity, SNAP SiNW sensors are capable of detecting parts per billion levels of an analyte. Peptides can be synthesized by the fluorenylmethoxycarbonyl (FMOC) solid phase peptide synthesis method, in which FMOC-protected amino acid residues are sequentially linked on a solid bead support via repeated cycles of coupling and deprotection. The peptides remain immobilized on the beads until cleaved by trifluoroacetic acid. Peptides can be subsequently purified to >95% by HPLC using a C18 semipreparative column. Peptides can then be immobilized onto the NWs using amide coupling. First, the nanowire surfaces are chemically modified by immersion of the chip in an amino silane (APTES) modifying reagent. Next, oligopeptides are synthesized with the desired recognition sequences, plus an aspartic acid "linking residue" tail at the carboxy terminus. The peptides can be dissolved in DMF, mixed with coupling reagents, and immediately injected into PDMS microfluidic chambers aligned to the device islands (FIG. 9). Once this coupling reaction is complete (2 h), the microfluidic channels are removed and the chip is thoroughly rinsed to remove any uncoupled peptide. Finally, the chip can be treated to a piperidine solution to cleave the FMOC protecting group. X-ray photoelectron spectroscopy (XPS) measurements on silicon-on-insulator (SOI)\wafer pieces, treated to identical surface reaction protocols as the SiNW sensors, can be employed to monitor this coupling chemistry.

SiNW Sensor Fabrication.

A typical set of NW sensors that can be employed for this biosensor is shown in FIG. 10. The chip containing the SNAP wire arrays can be treated to mild $O_2$ plasma (300 mTorr, 30 W, 60 s), then immersed in buffered oxide etch (BOE) for 3 s to remove oxides and promote the formation of ohmic contacts. Source and drain electrodes are formed by electron-beam evaporating 1000 Å Ti uniformly across the chip, and then patterning the Ti through a photoresist mask (Shipley 1813, MicroChem. Corp., Newton, Mass.) via wet etching (1:1:10 $HF/H_2O_2/DI$ v/v, 5 s). The resulting device channels are about 5 μm in length. A new photoresist mask can be applied to expose unwanted regions of the NW array for sectioning into device islands. The Si can be removed via reactive-ion etching (SF 6, 20 sccm, 20 mTorr, 30 W, 1 min), and the photoresist can be removed in acetone.

Fabrication of P-Type Doped Snap Nanowires

Silicon nanowires can be fabricated from an intrinsic, 320 Å thick SOI film ({100} orientation) with a 2,500 Å buried oxide. The substrate can be thoroughly rinsed and cleaned with deionized water then coated with p-type spin-on dopants. Dopants can be diffused into the SOI film using rapid thermal processing at 800° C. for 3 min. Analyzes with four-point resistivity measurements, correlated with tabulated values, shows a typical doping level of about $10^{18}$ cm$^{-3}$. Separately, a superlattice consisting of 800 layers of alternating GaAs and AlxGa(1−x) As thin films can be prepared. The superlattice can be cleaved along a single crystallographic plane and thoroughly cleaned by sonicating in methanol and gentle swabbing. The exposed edge can be immersed in $NH_3/H_2O_2/H_2O$ (1:20:750 v/v) for 10 s to selectively etch the GaAs regions (etch depth of about 30 nm). The resulting edge of the superlattice therefore consists of AlxGa(1−x) As plateaux separated by GaAs valleys. Pt metal can be deposited using electron-beam evaporation onto the edge of the AlxGa(1−x) As ridges, with the edge of the superlattice held at a 45° angle to the incident flux of Pt atoms. The Pt-coated superlattice edge can then be brought into contact with the doped SOI substrate spin-coated (6,000 r.p.m., 30 s) with a thin-film PMMA/epoxy (1:50 wt/wt). The superlattice/epoxy/SOI sandwich can be dried on a hot plate (150° C., 40 min), and the superlattice can be released by a selective etch in $H_3PO_4/H_2O_2/H_2O$ (5:1:50 v/v, 4.5 h) solution, leaving a highly aligned array of 400 Pt NWs on the surface of the SOI substrate. These Pt NWs serve as protective masks for a reactive ion etch process to produce aligned, single-crystal Si NWs ($CF_4$/He, 20/30 sccm., 5 mtorr, 40 W, 3.5 min). The Pt NWs can be dissolved in aqua regia (30 min) to produce an array of 400 Si NWs. Finally, the substrate can be cleaned in ALEG-355 solution to remove residual epoxy.

Among the various label-free signal transduction platforms that have been investigated, impedance spectroscopy is promising due to its simple instrumentation, ease of device assembly, and adaptability to multiplexed lab-on-a-chip applications. A microcapacitive sensor detects impedance changes in the dielectric properties of an electrode surface upon analyte binding, where the variation in the impedance is directly proportional to the activity of analyte binding.

Graphene/Silk Based Bioresorbable Passive Wireless Sensor

The operation and some functionalities possessed by our sensing technology is schematically illustrated in FIGS. 11A-D. FIG. 11A depicts an artistic illustration of the graphene based highly sensitive passive wireless biosensor element on a bioresorbable substrate of silk fibroin. The biosensor includes a wireless telemetry device 18 coupled to a sensor portion 20. In this example, the wireless telemetry device is a resonant circuit with an inductive coil. In this example the sensor portion 20 includes an immobilized peptide electrically coupled to an anode and a cathode. FIG. 11B illustrates the ability of these ultra-thin biosensors to be bioresorbed from the silk platform and intimately attached onto biological tissues, bones, or teeth through the dissolution of the supporting silk film for potential infectious agent monitoring. The high surface area of the graphene and electrodes ensures high adhesive conformability to the curvilinear surfaces of biological tissues such as skin or bone. Specificity in biological recognition is achieved through the integration of designer bifunctional peptides consisting of robust and naturally occurring antimicrobial peptide based biorecognition moieties assembled on to the graphene surface through combinatorially derived graphene binding peptide. The modification of antimicrobial peptides with peptide oligomers that bind to graphene enables the facile and non-covalent functionalization of the graphene nanomaterial transducers without affecting its excellent electronic properties. FIG. 11C illustrates the two other functionalities of the hybrid biosensor unit, particularly, battery free operation and remote wireless sensing capability. In this example, an antenna 22, e.g., a planar coil antenna, is disposed in proximity to the wireless telemetry device 18. A display unit 24 is coupled to the antenna 22. The display unit generally contains a transduction sensor configured to determine the conductivity of the biosensor. Upon the recognition and binding of specific bacterial targets by the immobilized antimicrobial peptides (FIG. 11D), the electrical conductivity of the graphene film changes, which can be wirelessly monitored using the inductively coupled radio frequency reader device 26. The presence of passive wireless components integrated with the resistive transducer enables the wireless interrogation of the sensor and any change in the conductance of the graphene layer is manifested as a modification of the fundamental electrical parameters of the oscillating circuit at resonance. This device can be used to remotely detect a wide variety of species, including, but not limited to, neuronal signaling networks, chemical threats such as TNT, bacteria on the skin or in the saliva via antimicrobial peptides, and/or disease metabolites which appear in the breath by implementing the sensor on a tooth.

Material Integration and Characterization

Figure 12:
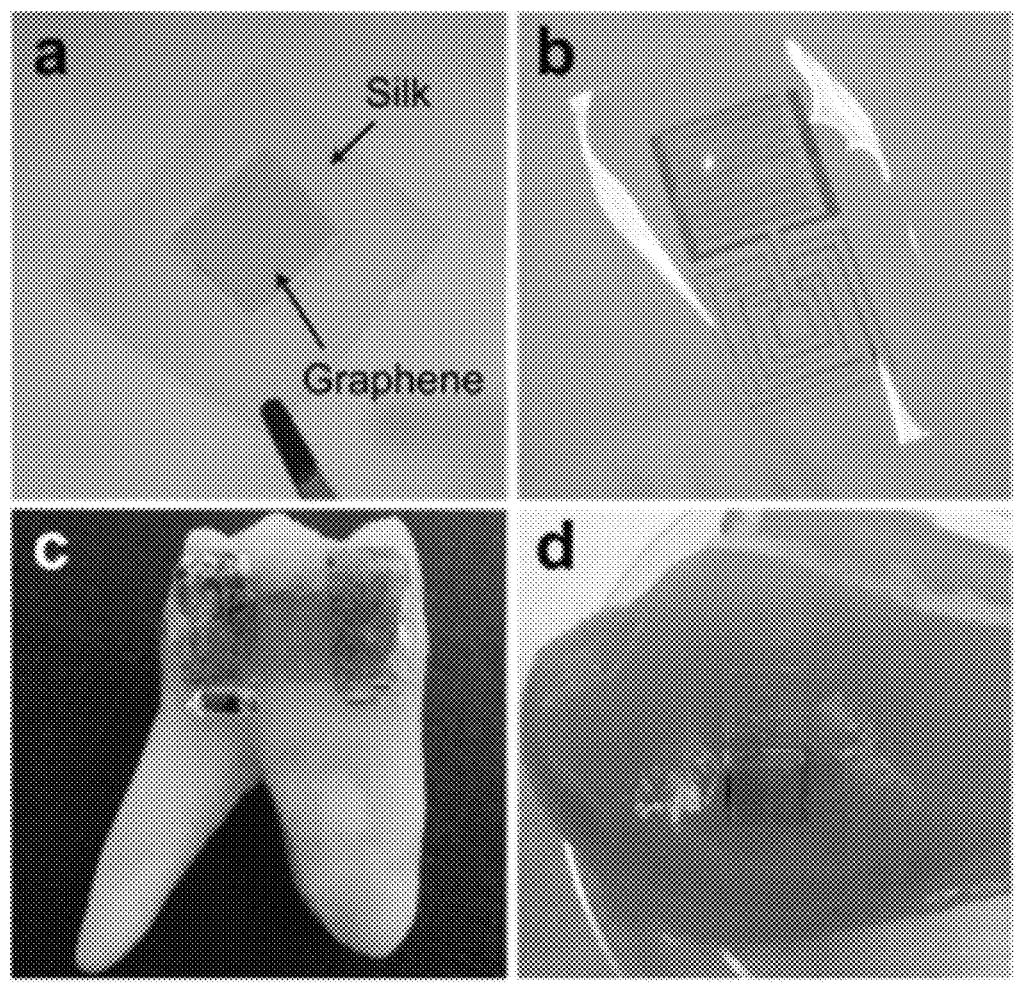
FIGS. 12A-F depict material integration and characterization for the biosensor.

Some functionalities of the graphene/silk hybrid sensing elements are derived from the synergistic integration of the smart properties possessed by its component materials. The biosensor interfaces passive wireless graphene nanosensors with biological substrates via bioresorbable silk substrates, including, but not limited to bone, teeth, and tissue. Large area, functional graphene nanomaterial transducers integrated with water soluble silk fibroin films of ca. 50 microns thick through a simple transfer printing process (FIG. 12A). It is possible for large-scale printing of graphene nanosensors onto silk substrates. Such techniques are demonstrated in Mannoor, M. S., Clayton, J. D., Tao, H., Omenetto, F. G., McAlpine, M. C. (2011) Graphene/Silk-Based Bioresorbable, Passive Wireless Sensors, manuscript submitted for publication, hereby incorporated by reference in its entirety.

Electrode patterns are incorporated on to the silk-graphene composite films through a shadow mask assisted electron beam evaporation of gold. FIG. 12B shows image of a graphene/silk hybrid biosensor device. The architecture consists of a parallel LRC resonant circuit with a gold inductive coil for wireless transmission, and interdigitated capacitive electrodes contacting sensitive graphene resistive sensors to form a passive wireless telemetry system, obviating the need for onboard power sources and any external connections. A full-wave electromagnetic simulation tool, Ansoft HFSS can be used to simulate and design various geometries of planar coil antenna and interdigitated capacitive electrodes.

The thin film sensing elements on silk platforms are then bioresorbed and intimately integrated on to a variety of substrates through the dissolution and removal of the supporting silk template. FIG. 12C shows the image of graphene nanomaterial with pattered gold electrodes integrated on to the surface of a human molar. Optical characterization of the graphene transferred on to $SiO_2$ surface through the dissolution of silk film revealed good structural integrity. FIG. 12D shows the image of the graphene/silk hybrid sensor bioresorbed on a tissue. Complete dissolution of silk matrix in water leading to the attachment of the graphene-Au electrode nanocomposite is observed with in a time period of 15-20 minutes.

Figure 12E:
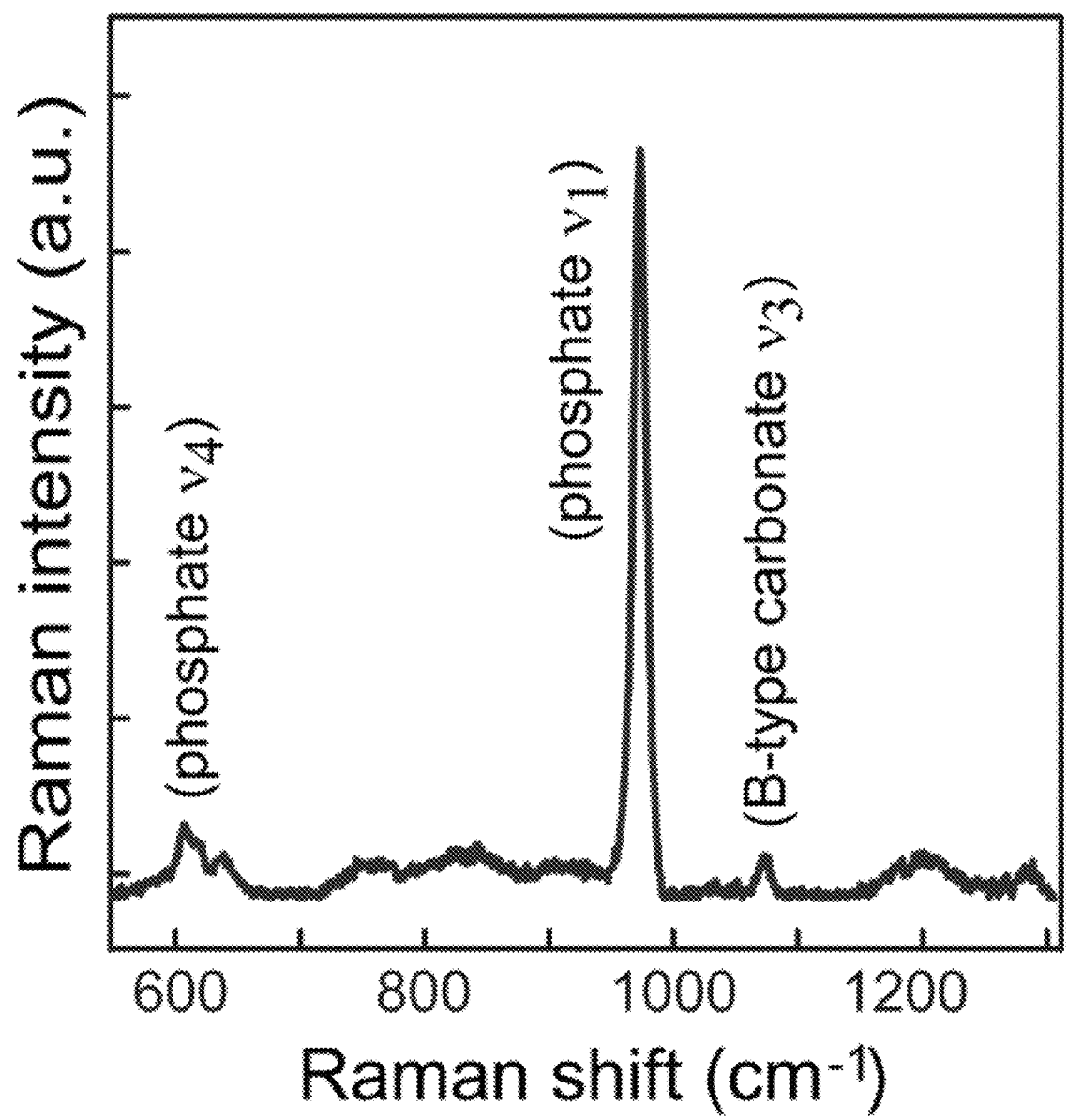
Figure 12F:
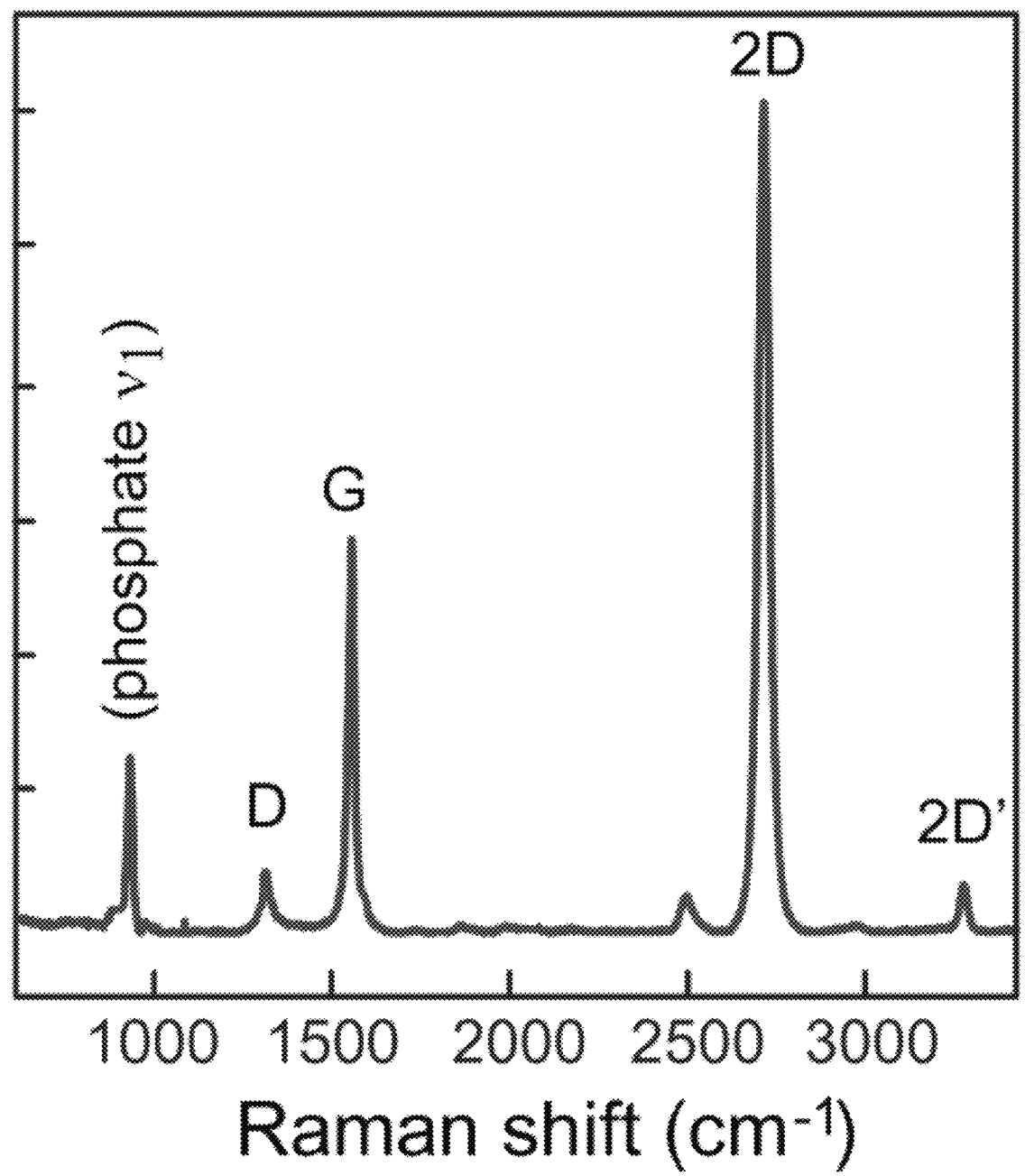

The electronic properties and structural information of the graphene integrated with the tooth surface is investigated using Raman spectroscopy studies. FIG. 12E shows the Raman spectrum of a tooth surface before the integration of graphene nanosensor. FIG. 12F shows the spectrum of the graphene nanosensor integrated on to the tooth surface via bioresorption of silk substrate.

Single Bacterium Detection

To demonstrate the response of the graphene-nanosensors towards single bacterial cells and to characterize the sensitivity of the graphene transducing element, simultaneous electrical and optical measurements were conducted. Time dependent resistance data recorded simultaneously with optical measurements on graphene nanosensors showed discrete changes in the graphene resistance in the presence of a sample of approximately 100 bacterial cells per µL loaded on to the sensor elements by pipette (see FIG. 13A). Simultaneous collection of electrical and fluorescence data from the graphene sensors in the presence of fluorescently labeled *E. coli* cells clearly indicate that the change in the resistance recorded corresponds to the binding and unbinding of the bacterial cell from the graphene surface. The resistance of the graphene sensor remains at the baseline value until the bacterial cell diffuses to the sensor surface and drops down by approximately 0.6 percentage of the original, once the bacterial cell binds to the graphene surface.

The resistance of the sensor decreases from the baseline value up on the binding of the negatively charged bacterial cell and returns back to the initial value up on unbinding, indicating a p-type behavior of the graphene transducer. The ability to specifically distinguish between various species of pathogenic bacteria is important in utilizing the high sensitivity of the graphene nanosensors in most medical and biorecognition applications. In is contemplated that biocombinatorial screening techniques such as phage display can be used to determine peptide sequences which selectively bind to graphene. In order to impart selectivity to the sensing mechanism, graphene transducers were functionalized with antimicrobial peptide O-HP which has been identified to show specific activity toward both Gram-negative bacteria (*E. coli* and *H. pylori*) and Gram-positive bacteria (*S. aureus*). Facile and efficient assembling of the antimicrobial peptides on the graphene nanosensors were enabled by generating bifunctional peptides that link the graphene binding motif and O-HP separated by triglycine, resulting in the 38 amino acid sequence, HSSYWYAFNNKT-GGG-GLLRASS-VWGRKYYVDLAGCAKA (SEQ ID NO: 20) (FIG. 13B). The triglycine linker provides flexibility and independent accessibility of the bacterial cells towards the O-HP. In order to determine the effect of the immobilized AMPs on the binding/unbinding properties simultaneous resistance and optical data were recorded on graphene sensors functionalized with antimicrobial peptides. Continuous binding of bacterial cell without unbinding for a much longer time period compared to the duration of binding in the case of non-functionalized graphene was observed (FIG. 13C). This shows that the immobilized peptide (O-HP) slows the unbinding kinetics of the bacterial cells. FIG. 13C inset shows the fluorescent image of the graphene-interdigitated electrode nanosensor functionalized with FITC-labeled antimicrobial peptides.

For the purpose of determine the location of the binding motif within the peptide, a bifunctional peptide sequence with the antimicrobial peptide in an inverted fashion was synthesized. Binding density analysis with fluorescently labeled bacterial cells did not show any significant difference in the binding affinity between the normal and inverted O-HPs, indicating that the sequences responsible for the bacterial binding is present at the middle of the AMP sequence.

Wireless remote-query monitoring of *S. aureus* and *H. pylori*. One functionality of the graphene/silk hybrid sensing element is the wireless remote-query capability. *Staphylococcus aureus*, a Gram-positive pathogenic bacteria found on skin flora and hospital environments, is notoriously drug-resistant and responsible for over 500,000 post-surgical wound infections in the US per year. To simulate the use of the graphene wireless sensor in hospital sanitation and biohazard monitoring, the sensing elements were integrated on to an intravenous (I.V.) bag through the dissolution of the supporting silk substrate (FIG. 14A). *S. aureus* has been reported to survive up to 9 weeks on standard plastic and similar dry hospital environments. To demonstrate the capability of the biosensor to detect *S. aureus* in typical hospital conditions, 1 µL solutions containing various concentrations ($10^3$-$10^8$ cfu/mL) bacterial cells were delivered to the biosensor and allowed them to dry on the biosensor surface for 30 min. The change in the graphene resistance up on bacterial binding is wirelessly monitored as the bandwidth change in the sensor resonance curve. FIG. 14B plots the bandwidth of the sensor corresponding to the different concentration of the *S. aureus* cells incubated on the sensor surface. The percentage change in graphene resistance is calculated from the bandwidth and is depicted in FIG. 14C.

In order to demonstrate the performance of the sensor directly integrated with biological tissue, creating the possibility for on-body health quality monitoring, the wireless sensing elements were bioresorbed and integrated on to the surface of a tooth (FIG. 14D). This embodiment of the biosensor enables the remote monitoring of the presence of infectious agents in saliva and disease metabolites in breath. To this end, the response of the graphene hybrid sensors to *Helicobacter pylori*—a Gram-negative species found in the stomach and saliva which is estimated to be responsible for the development of over 90% of duodenal ulcers and stomach was analyzed. Real-time change in graphene resistance up on exposure to various concentrations of *H. pylori* cells in DI water was monitored by recording the characteristic frequencies at resonance. FIG. 14E depicts the real-time change in graphene resistance up on the exposure to a 1 µL sample containing ~100 *H. pylori* cells. The sensor resistance is observed to be stabilized after around 10 to 15 min. The response of the graphene sensing element to 1 µL of "blank" DI water without any bacterial cells is used as a control. FIG. 14F depicts the percentage change in resistance as a function of bacterial concentration. A linear relationship is observed between the logarithm of bacteria concentration and the resistance change up to a concentration of $10^6$ bacterial cells.

Summary of Nanoscale Biosensor

The biosensor in its nanoscale embodiment is the first example of a practical realization of the direct integration of functional material—graphene nanosensors—with human body to function as a standalone biological sensor. A bioresorbable sensor for highly sensitive and selective detection of biological analytes is realized through the synergistic integration of the smart properties of selectivity in biological recognition possessed by naturally occurring antimicrobial peptides with the high sensitivity of two dimensional graphene nanomaterial transducers on a biocompatible silk fibroin substrate. The incorporation of a parallel resonant circuit with a gold thin film patterned meander line inductor and interdigitated capacitive electrodes form a passive wireless telemetry system that eliminates the need for onboard power sources and any external connections. The thin film sensing elements on silk platforms can be bioresorbed and intimately integrated on to biological tissues, bones or teeth. The nanometer size scale and large surface area of the sensing elements allows it to conform to the curvilinear surfaces biological tissues or bone. Gradual bioresorption of the supporting silk films leaves the ultra-thin sensors intimately in place allowing sensitive detection of target analytes and subsequent wireless read-out.

Silk thin films serve as the preferred temporary platform for the sensing elements due to their optical transparency, mechanical robustness, bioresorbability, flexibility and biocompatibility. When crystallized in air, silk fibroin secondary structure kinetically favors silk I formation, a disordered collection of α-helices and random coils resulting in aqueous solubility. Silk I thin films are flexible, biocompatible, and possess programmable solubility rates dependent on externally induced β-sheet content and fibroin concentration, making them ideal substrates for the clean transfer of graphene to biological and material surfaces.

Functionalization of the graphene nanosensors with bifunctional peptides consisting of biocombinatorially derived graphene binding motif linked with robust and naturally occurring antimicrobial peptide based biorecognition moieties enables selective and efficient recognition of pathogenic bacteria. Non-covalent modification of graphene with biocombinatorially derived peptides through rigorous phage display screening provides a general approach for the selective functionalization of graphene without modifying its excellent properties. Assembling of the designer bifunctional peptides with specific binding domains offers a simple and versatile means to integrate the smart property of specificity in biological recognition possessed biological macromolecules with the highly sensitive signal transduction capability of graphene nanosensors. The isolation of graphene-binding peptides (GBP) through phage display reveals high surface coverage and strong binding activity, which occurs through p-stacking interactions between aromatic residues. Graphene sheets functionalized with Odorranin-HP, an antimicrobial peptide isolated from the skin of the frog species *Odorrana grahami*, enable simultaneous detection of Gram-positive and Gram-negative bacteria species. Bacterial binding of AMPs are observed as precursor to their bacteriocidal activity. O-HP in particular shows potent activity against *Helicobacter pylori* (MIC: 20 ug/mL), a Gram-negative species found in the stomach and saliva which is estimated to be responsible for the development of over 90% of duodenal ulcers and stomach cancers; *Staphylococcus aureus* (MIC: 5 ug/mL), a Gram-positive species found on skin flora and hospital equipments which is notoriously drug-resistant and responsible for over 500,000 post-surgical wound infections in the US per year; and *Escherichia coli* (MIC: 30 ug/mL), a Gram-negative species found in the lower intestine of endotherms with known strains capable of acute food poisoning and urinary tract infections resulting from unhygienic meat and dairy preparation. O-HP is also known to exert antimicrobial activity against methicillin resistant strains of *S. aureus*.

A single layer thin film inductor-capacitor (LC) resonant circuit integrated in parallel combination with the resistive graphene monolayer enables wireless read-out and battery-free operation. The change in conductance of the graphene nanosensor up on the binding of pathogenic bacteria to the immobilized AMPs is resolved from change in the characteristic frequencies and bandwidth of sensor resonance.

The characteristic frequencies and the bandwidth are quantities that are inherent to the resonant circuit and do not depend on the mutual inductance (coupling coefficient) between the sensor and the reader coil. Therefore the relative alignment and location of the biosensor with respect to the reader antenna is not important during measurements.

In one embodiment of the biosensor, the direct integration of the highly sensitive graphene nanosensors with human body and other analyte substrates of importance such as an IV bag, to function as a fully standalone, battery free biological sensors for the remote monitoring of pathogenic bacteria and other biothreat agents fulfills a long-desired need in bio- and chemical analysis. It is contemplated the demonstrated biosensor can be combined with other known biological binding proteins, peptides and motifs to provide biological and chemical detection systems for applications including, diagnostics, hospital sanitation monitoring and food safety analysis.

In another embodiment of the nanoscale form of the biosensor the biosensor is comprised of as few components as bare graphene fashioned into a sensor combine with a passive wireless transmitter printed on a bioresorbable substrate. In this form the biosensor can be situated on nearly any biologic substrate, or any other substrate capable of bioresorption, for a non-limiting example: cheese. This particular embodiment is not limited to combination with antimicrobial peptides, but can be used with an detection molecule capable of creating a variance in impedance including but not limited to antibodies, DNA fragments, RNA fragments, peptide binding motifs, and polymers. In perhaps the most basic for of the nanoscale embodiment of the biosensor it has been demonstrated that the biosensor featuring only a wireless passive transmitter and a bare microarray without any specific detection molecules attached is able to detect human breath in real time.

It is then further contemplated that in certain of these types of embodiments of the biosensor the biologic binding molecule is a glucose transporter (for non-limiting examples GLUT1, GLUT2, GLUT3, and GLUT4) or a glucose transporter glucose-binding motif (for non-limiting examples the glucose-binding motif of GLUT1, GLUT2, GLUT3, and GLUT4). In these embodiments the biosensor is capable of detecting the presence and concentration of glucose in a sample, for instance a blood sample. It is yet further contemplated that certain types of these embodiments the biosensor could be injected intravenously, implanted intravenously or implanted on a body tissue in contact with blood inside a body. In these particular embodiments, the biosensor could be able to bind glucose in the blood and transmit the variance of impedance to an external receiver that could calculate the concentration of glucose in the blood and display this concentration on the display unit.

It is also contemplated that other certain types of these embodiments of biosensor can be constructed with multiple circuits each comprising a microarray, a wireless telemetry unit and a binding molecule laid on a single substrate of a bioresorbable material. In these embodiments the biosensor can comprise a plurality circuits with different binding molecules. For non-limiting instance, it is contemplated that one embodiment of the biosensor may comprise a plurality of circuits comprising a binding molecule that binds one of following targets: *E. Coli* bacteria, *Staphylococcus* bacteria, Rh factor, bile, meconium, markers of meconium, herpes bacteria and, optionally, a circuit that comprises microarray, a wireless telemetry unit and a carbon microphone, a capsule containing carbon granule situated between to metal plates, electrically coupled to the microarray. This embodiment when implanted in the vagina or cervical canal of a pregnant female the biosensor acts as an internal fetal monitor, monitoring for a variety of potential fetal infections, complications and optionally heartbeat.

Therefore, it is contemplated that the nanoscale embodiment of the biosensor can be combined with virtually any known sensing molecule including but not limited to, antimicrobial peptides, antibodies, modified antimicrobial peptides, modified antibodies, chimeric peptides containing antimicrobial peptide binding motifs, chimeric peptides containing antibody binding motifs, DNA fragments, RNA fragments, peptide binding motifs, proteins, small molecules and polymers combinations thereof.

EXAMPLES

Example 1

Antimicrobial Peptides and Bacterial Cells

Antimicrobial peptide magainin I (GIGKFLHSAGKF-GKAFVGEIMKS) (SEQ ID NO: 1), chemically synthesized to contain a C-terminal cysteine residue via standard N-fluorenylmethoxycarbonyl (FMOC) solid phase peptide synthesis, was obtained from Anaspec (San Jose, Calif.). Magainin I was also custom synthesized with an N-terminal Cysteine to compare the bacterial binding activity. Heat-killed pathogenic bacterial cells of *E. coli* O157:H7, *Salmonella typhimurium* and *Listeria monocytogenes* were purchased from KPL (Gaithersburg, Md.). Heat-killed cells of a non-pathogenic strain of *E-Coli* (ATCC 35218) was obtained from American Type Cell Culture (ATCC, Manassas, Va.) for a control. The stock solution of AMP was prepared by the reconstitution of the lyophilized product in phosphate buffered saline (Sigma-Aldrich, St. Louis, Mo.) consisting of 137 mM NaCl, 2.7 mM KCl, 4.4 mM $Na_2HPO_4$ and 1.4 mM $KH_2PO_4$ (pH 7.4). The heat-killed bacterial cells were rehydrated in PBS, according to ATCC recommendations.

The bifunctional peptide GBP-GGG-OHP (HSSYW-YAFNNKT-GGG GLLRASSVWGRKYYVDLAGCAKA) (SEQ ID NO: 20) containing a graphene binding motif linked to the antimicrobial peptide OHP through a triglycine linker were chemically synthesized and obtained from Peptide 2.0 Inc., (Chantilly, Va.). The peptides were also custom synthesized with the antimicrobial peptide linked in an inverted fashion to compare the bacterial binding activity. Heat-killed pathogenic Gram-negative bacterial cells of *E. coli* O157:H7 and *H. pylori* were purchased from KPL (Gaithersburg, Md.). Heat-killed Gram-positive bacterial cells of *S. Aureus* were purchased from Invitrogen Inc. The stock solution of peptide was prepared by the reconstitution of the lyophilized powder in DI water. Different concentrations of bacterial samples were prepared from stock solutions by dilutions in deionized water. Phosphate buffered saline consisting of 137 mM NaCl, 2.7 mM KCl, 4.4 mM $Na_2HPO_4$ and 1.4 mM $KH_2PO_4$ (pH 7.4), $FeCl_3$, Sodium carbonate and Lithium bromide for the processing of silk is purchased from Sigma-Aldrich (St. Louis, Mo.).

Example 2

Interdigitated Microelectrode Array (IMA) and Microfluidic Flow Cell

Interdigitated capacitive electrodes were microfabricated on 4" p-type silicon wafers (boron-doped, <100>, 10-16 Ω-cm, 550 µm thick). A 1 µm thick silicon dioxide layer was deposited on the wafer by plasma enhanced chemical vapor deposition (PECVD) to form electrical insulation between the Si substrate and the capacitive electrodes. S1813 photoresist was patterned using photolithography, followed by electron-beam evaporation of 10 nm Ti and 300 nm Au under high vacuum conditions. The titanium layer helps to provide adhesion of the Au to the $SiO_2$. The IMA was then finally developed by lift-off patterning of the metallic layer in acetone with ultrasonic activation. The electrode array consisted of 50 pairs of interdigitated capacitive electrodes with an electrode width and separation of 5 µm. A polydimethylsiloxane (PDMS) microfluidic flow cell consisting of a detection microchamber with an embedded microelectrode array, inlet and outlet ports was formed by bonding the IMA chip to the PDMS channel. The PDMS micro-channel formed on the master mold was partially cured, aligned with the microelectrode array and bonded by permanently curing at 80° C. for 2-3 hr. Microfluidic connectors were fixed on to the inlet and outlet ports through drilled holes.

Example 3

Sensor Surface Functionalization with Magainin

The immobilization of the peptides to a gold surface was performed a technique utilizing the native thiol groups present in cysteine residues. Furthermore, cysteine residues can be synthetically introduced in to a specific site of the peptide to form a properly oriented recognition layer. Magainin I was synthesized both with a C-terminal and N-terminal cysteine via FMOC solid-phase synthesis. Prior to the immobilization procedure, the gold IMA electrodes were cleansed using acetone, isopropanol and deionized water. Stock solutions of the AMPs were prepared in phosphate-buffered saline (PBS), pH 7.4, consisting of 137 mM NaCl, 2.7 mM KCl, 4.4 mM $Na_2HPO_4$ and 1.4 mM $KH_2PO_4$. For the immobilization of the AMPs, 800 µg/ml (unless otherwise mentioned) of magainin I in PBS buffer was injected into the sensing chamber and incubated for 60 min under static conditions. The functionalized electrodes were then rigorously washed with 1×PBS to remove any unbound AMPs, rinsed with de-ionized water and dried in liquid nitrogen.

Example 4

Fluorescent Microscopy

Stock solutions of propidium iodide (PI), nucleic acid stain (Molecular probes, Eugene, Oreg.) were made from solid form by dissolving PI (MW=668.4) in deionized water at 1 mg/mL (1.5 mM) and stored at 4° C., protected from light. Heat-killed bacterial cells rehydrated in PBS were then incubated with 3 μM solution of propidium iodide, PI (made by diluting the 1 mg/mL stock solution 1:500 in buffer) for 10-15 min (51). After incubation, the cells were centrifuged into pellets, the supernatant was removed and the cells were resuspended in fresh 1×PBS buffer. The samples of stained bacterial cells (*E. coli* O157: H7, *Salmonella*, non-pathogenic *E. coli* and *Listeria*, all $10^7$ CFU/mL) were then allowed to incubate with the immobilized Magainin for 15-20 min in the dark. After incubation, the Au surfaces were washed with PBS buffer and dried under liquid nitrogen. The binding pattern of the different bacterial cells was imaged using a Zeiss axiovert inverted microscope and recorded with a Zeiss axiocam digital camera. Surface density of the bound bacterial cells was analyzed and plotted using imageJ software from NIH.

Example 5

Impedance Spectroscopy

Dielectric property changes due to AMP-bacteria interactions were probed using a Fast-Fourier Transform (FFT) spectrum analyzer. The dielectric properties were investigated over a frequency range of 10 Hz to 100 kHz, with 0 V DC bias and 50 mV AC signals using a SRS 785, 2-channel dynamic signal analyzer. The LabView program routine was used to collect and record the data through a GPIB interface. An external op-amp amplifier circuit was used to minimize the noise and a MATLAB program was used to plot the impedance spectra from the analyzer output (see supplementary information FIG. S1). For sensitivity measurements, pathogenic Gram-negative *E. coli* O157:H7 bacterial cells were injected into the microfluidic flow channel at various dilutions, and incubated with the immobilized magainins for 12-15 min, under static conditions. To ensure the response of the sensor toward bound bacterial cells, the impedance spectrum was taken after the removal of unbound cells by thorough washing in PBS. For real-time measurements, the impedance vs. time data was recorded while buffer solutions or different dilutions of bacterial solutions flowed through the microfluidic channel. The flow cell was first flushed with 1×PBS buffer at a flow rate of 100 μL/min to establish a baseline. Bacterial detection measurements were performed with the sample flowing at a rate of 5 μL/min. The main effect of the bacterial cells bound to the immobilized magainins on the impedance signal is due to the dielectric property of the cell membrane.

Example 6

Silk Films

Silk solutions are versatile and can be prepared in various forms including electrospun fibers, films, gels and sponges, all having tunable properties such as solubility, elasticity and biodegradability. Silk from the domesticated silkworm, *Bombyx mori*, is perhaps the most useful type due to its availability. *B. mori* cocoons are primarily composed of two types of protein: fibroin and sericin. The fibroin fibers, consisting of a heavy and light chain connected by a disulfide bond, are responsible for the structural integrity of the cocoons. The fibroin protein consists of layers of antiparallel beta sheets, largely responsible for the tensile strength of the material. Its primary structure mainly consists of the recurrent amino acid sequence (Gly-Ser-Gly-Ala-Gly-Ala)n (SEQ ID NO: 21). The fibers are enveloped by the hydrophilic protein sericin, which acts as a sticky glue holding the cocoon together. An outer coating provides extra protection from microbes and predators.

In order to extract the desired fibroin protein, the sericin was removed by boiling cleaned cocoons in 0.02 M $Na_2CO_3$ for 30 minutes followed by thoroughly rinsing with water. The degummed silk was then dissolved in 9.3M aqueous lithium bromide and the solution is dialyzed to remove excess salt. The resulting aqueous solutions are 6-10% (w/v) fibroin and can be preserved by storage at 5° C. Silk films were made by casting fibroin solutions onto PDMS and drying in air for 12-24 h, depending on the thickness. When crystallized in air, silk fibroin secondary structure kinetically favors silk I formation, a disordered collection of a-helices and random coils resulting in aqueous solubility.

Silk I thin films are flexible, biocompatible, and possess programmable solubility rates dependent on externally induced b-sheet content and fibroin concentration, making them ideal substrates for the clean transfer of graphene to biological and material surfaces.

Example 7

Fabrication of Silk/Graphene Wireless Sensing Elements

Bioresorbable, thin film sensing elements can be patterned on to water soluble silk fibroin films of ca 50 microns thick through a series of simple fabrication steps. First, dissolvable films of silk were cast directly from aqueous *Bombyx mori* (dissolved cocoons of silk worms) silk solutions to serve as bioresorbable substrates. CVD grown graphene monlolayers from Ni thin films were released and transferred on to PDMS stamps by the removal of Ni layer in $FeCl_3$ and are then transfer printed on to the silk films. Clean transfer of graphene monolayers on to silk was achieved through controlled moistening of the silk surface. Planar inductive and capacitive elements were then incorporated on to the graphene/silk samples to enable wireless interrogation capability. A meander line design for the inductive element allowed planar implementation of the wireless telemetry unit, integrated on to the graphene nanosensor via a shadow mask assisted one step evaporation electron beam evaporation of gold. The thin film sensing elements on silk platforms were then bioresorbed and intimately integrated on to surfaces such as biological tissues, bones or teeth.

Example 8

Bioresorption

Integration of the wireless sensing elements on to tooth surface was achieved through the dissolution of the supporting silk substrate. The surface of the tooth was first cleaned and dried with a low-particulate clean room wipe. In the case of teeth, and other such dry surfaces, a moistened cotton swab was used to slightly wet the surface. The graphene-Au electrode sensing elements on the temporary silk films were then carefully aligned and placed on the tooth surface with the device side facing down. The temporary silk film platform was then gradually dissolved off by the application of water, leaving the ultra-thin sensors intimately attached to the surface of the tooth. The integration of the sensing elements on to the surface of the I.V. bag was also done similar to the above procedure. In the case of wet surfaces of biological tissue and food materials such as cheese, the dissolution of the silk film was observed to be faster. The high surface area of the graphene and electrodes ensures high adhesive conformability to the curvilinear surfaces in biological tissues such as skin or tooth.

Example 9

Graphene Functionalization with Antimicrobial Peptide O-HP

In functionalizing graphene sheets, a peptide that links GBP and O-HP via triglycine was generated, resulting in the 38 amino acid sequence, HSSYWYAFNNKT-GGG-GLL-RASSVWGRKYYVDLAGCAKA (SEQ ID NO: 20): The GBP-GGG-O-HP bifunctional peptide. These peptides were dissolved in deionized water at a concentration of 1 mg/mL. Five microliters of the peptide solutions were dropped onto the graphene and incubated for 15 min, followed by washing with deionized water and drying.

Example 10

Single Bacterium Detection Measurements

Electrical measurements for the detection of single bacteria binding measurements were performed with a lock-in detection system using Stanford Research Systems 810 DSP lock-in amplifier. A modulation signal of 50 mV was used with a modulation frequency of 73 Hz with zero DC bias to avoid any electrochemical reactions. The resistance of the graphene sensor was monitored continuously in the presence of analyte sample of various dilutions of bacterial cells.

Bacterial cells for the simultaneous optical monitoring and for the antimicrobial peptide-bacteria binding density studies are fluorescently labeled with propidium iodide using known methods. Stock solutions of propidium iodide (PI), nucleic acid stain (Molecular probes, Eugene, Oreg.) were made from solid form by dissolving PI (MW=668.4) in deionized water at 1 mg/mL (1.5 mM) and stored at 4° C., protected from light. Heat-killed bacterial cells rehydrated in PBS were then incubated with 3 µM solution of propidium iodide, PI (made by diluting the 1 mg/mL stock solution 1:500 in buffer) for 10-15 min. After incubation, the cells were centrifuged into pellets, the supernatant was removed and the cells were re-suspended in DI water or 1×PBS buffer. The binding pattern of the different bacterial cells was imaged using a Zeiss axiovert inverted microscope and recorded with a Zeiss axiocam digital camera. For the real-time detection of single bacterial cell (*E. coli* 0157: H7) a sample containing 100 bacterial cells per µL was loaded by pipette on to the graphene sensors. Simultaneous bright field and fluorescent data were recorded together with lock-in resistance data with the focal plane set on the graphene surface to identify the events when the bacterial cells come close to the sensor. The motion of the bacterial cells were tracked relative to the position of the graphene surface with the help of video spot tracker, a freely available automated tracking software and also with the manual tracking plugin in the National Institutes of Health's ImageJ software.

Example 11

Wireless Sensing

An inductive-capacitive (LC) resonant circuit, integrated in parallel with the resistive graphene monolayer, forms the basis of the wireless read-out unit. The reader device consists of a two-turn coil antenna connected to a frequency response analyzer (HP 4191A RF impedance analyzer). The wireless reader, which is powered by an alternating current source, is responsible for wirelessly transmitting power and receiving sensor data from the remote passive sensor, all through inductive coupling. Passing an AC signal through the antenna generates a magnetic field, e.g., reference number 28, FIG. 11C, inducing current via mutual inductance in the coil of the sensing element (Faraday's law), finally resulting in a potential drop that depends on the conductance of the graphene nanosensor. Any change in the conductivity of the sensor system resulting from biological or chemical changes happening at the transducer surface will be reflected as a change in the fundamental properties—characteristic frequencies and the bandwidth—at resonance. This allows the reader to wirelessly interrogate the sensing element via the complex impedance of the system. The equivalent circuit of the sensing element can be used to calculate the bandwidth of the reader-sensor system and the input impedance of the system as viewed by the reader device. The change in the capacitance of the graphene-interdigitated electrode sensing system is deduced from the resonance frequency shift, the expression for which is as follows:

$$\Delta f = \frac{1}{2\pi\sqrt{L*\Delta C}} \qquad (2)$$

The bandwidth of the sensor resonance is measured from the resonance peaks and was used to calculate the change in resistance (conductance) of the graphene-electrode sensing element up on the binding of the bacterial cells. The expression for the change in resistance of the system is as follows:

$$\Delta R = 1/(2\pi*\Delta C*\Delta B) \qquad (3)$$

Detailed description of the calculation of the system bandwidth is provided in the supporting information. The characteristic frequencies of the sensor system can be measured by monitoring the complex impedance spectrum of the system. The frequency at which the imaginary part of the sensor impedance vanishes (reactance X=0) is continually monitored and used to calculate the change in the graphene conductance.

$$\Delta R = \left(\frac{L}{\Delta C(1 - 2\pi*\Delta f_z)L*\Delta C}\right)^{1/2} \qquad (4)$$

Although features and elements are described above in particular combinations, each feature or element may be used alone without the other features and elements or in various combinations with or without other features and elements.

What is claimed is:

1. A biosensor configured for application to a biological surface, the biosensor comprising:
 a microelectrode array disposed on a dissolvable substrate;
 an anode and a cathode electrically coupled to the microelectrode array;
 a resonant circuit with an inductive coil electrically coupled to the cathode and anode; and
 a wireless telemetry unit electrically coupled to the resonant circuit, forming an electric circuit,
 the dissolvable substrate being configured to be dissolved off by the application of water, leaving the microelectrode array, resonant circuit and wireless telemetry unit intimately attached to the biological surface.

2. The biosensor of claim 1, further comprising:
 a binding molecule disposed on the microelectrode array, the microelectrode array having an electrical conductivity that is dependent on a binding state of the binding molecule.

3. The biosensor of claim 2, wherein binding molecule is selected from the list consisting of: antimicrobial peptides, antibodies, modified antimicrobial peptides, modified antibodies, chimeric peptides containing antimicrobial peptide binding motifs, chimeric peptides containing antibody binding motifs, DNA fragments, RNA fragments, peptide binding motifs, proteins, small molecules and polymers combinations thereof.

4. The biosensor of claim 1, wherein the dissolvable substrate is selected from a list consisting of: poly(ethylene terepthalate), poly(imide), poly(ether sulfone), cellulose, paper, silk, silk fibroin and combinations thereof.

5. The biosensor of claim 1, wherein the dissolvable substrate is placed in contact with a biologic surface.

6. The biosensor of claim 5, wherein the biologic surface is capable of bioresorption.

7. The biosensor of claim 5, wherein the biologic surface is selected from the list consisting of: teeth, bone, skin, tissue, hair, nail, cornea, gum, tongue, palate, brain, heart, lung, membrane, leaf, root, bark, fur, feather, chiton and scale.

8. The biosensor of claim 1, further comprising:
 a receiver unit having a planar coil antenna electrically coupled to a readout, the planar coil antenna being configured to power the electric circuit, enabling the wireless telemetry unit to send a wireless signal corresponding to an electrical conductivity of the circuit to the receiver unit, the readout being responsive to changes in the electrical conductivity of the circuit.

9. The biosensor of claim 1, wherein the binding molecule is contains a glucose-binding motif.

10. The biosensor of claim 1, wherein the microelectrode array is interdigitated.

11. The biosensor of claim 1, wherein the microelectrode array comprises graphene.

* * * * *

SEQUENCE LISTING

<160> NUMBER OF SEQ ID NOS: 21

<210> SEQ ID NO 1
<211> LENGTH: 23
<212> TYPE: PRT
<213> ORGANISM: Unknown
<220> FEATURE:
<223> OTHER INFORMATION: Description of Unknown: Antimicrobial
      peptide

<400> SEQUENCE: 1

Gly Ile Gly Lys Phe Leu His Ser Ala Gly Lys Phe Gly Lys Ala Phe
1               5                   10                  15

Val Gly Glu Ile Met Lys Ser
            20

<210> SEQ ID NO 2
<211> LENGTH: 21
<212> TYPE: PRT
<213> ORGANISM: Unknown
<220> FEATURE:
<223> OTHER INFORMATION: Description of Unknown: Antimicrobial
      peptide

<400> SEQUENCE: 2

Gly Leu Phe Gly Lys Ile Leu Gly Val Gly Lys Lys Val Leu Cys Gly
1               5                   10                  15

Leu Ser Gly Met Cys
            20

<210> SEQ ID NO 3
<211> LENGTH: 38
<212> TYPE: PRT
<213> ORGANISM: Unknown
<220> FEATURE:
<223> OTHER INFORMATION: Description of Unknown: Antimicrobial
      polypeptide

<400> SEQUENCE: 3

Arg Leu Lys Glu Leu Ile Thr Thr Gly Gly Gln Lys Ile Gly Glu Lys
1               5                   10                  15

Ile Arg Arg Ile Gly Gln Arg Ile Lys Asp Phe Phe Lys Asn Leu Gln
            20                  25                  30

Pro Arg Glu Glu Lys Ser
            35

<210> SEQ ID NO 4
<211> LENGTH: 62
<212> TYPE: PRT
<213> ORGANISM: Unknown
<220> FEATURE:
<223> OTHER INFORMATION: Description of Unknown: Antimicrobial
      polypeptide

<400> SEQUENCE: 4

Asn Arg Trp Tyr Cys Asn Ser Ala Ala Gly Gly Val Gly Gly Ala Ala
1               5                   10                  15

Gly Cys Val Leu Ala Gly Tyr Val Gly Glu Ala Lys Glu Asn Ile Ala
            20                  25                  30

Gly Glu Val Arg Lys Gly Trp Gly Met Ala Gly Gly Phe Thr His Asn
            35                  40                  45

Lys Ala Cys Lys Ser Phe Pro Gly Ser Gly Trp Ala Ser Gly
    50                  55                  60

```
<210> SEQ ID NO 5
<211> LENGTH: 43
<212> TYPE: PRT
<213> ORGANISM: Unknown
<220> FEATURE:
<223> OTHER INFORMATION: Description of Unknown: Antimicrobial
      polypeptide

<400> SEQUENCE: 5

Lys Tyr Tyr Gly Asn Gly Val Ser Cys Asn Lys Gly Cys Ser Val
1               5                   10                  15

Asp Trp Gly Lys Ala Ile Gly Ile Ile Gly Asn Asn Ser Ala Ala Asn
                20                  25                  30

Leu Ala Thr Gly Gly Ala Ala Gly Trp Lys Ser
            35                  40

<210> SEQ ID NO 6
<211> LENGTH: 32
<212> TYPE: PRT
<213> ORGANISM: Unknown
<220> FEATURE:
<223> OTHER INFORMATION: Description of Unknown: Antimicrobial
      polypeptide

<400> SEQUENCE: 6

Gly Leu Trp Ser Lys Ile Lys Glu Ala Ala Lys Ala Ala Gly Lys Ala
1               5                   10                  15

Ala Leu Asn Ala Val Thr Gly Leu Val Asn Gln Gly Asp Gln Pro Ser
                20                  25                  30

<210> SEQ ID NO 7
<211> LENGTH: 68
<212> TYPE: PRT
<213> ORGANISM: Unknown
<220> FEATURE:
<223> OTHER INFORMATION: Description of Unknown: Antimicrobial
      polypeptide

<400> SEQUENCE: 7

Ala Glu Leu Arg Cys Met Cys Ile Lys Thr Thr Ser Gly Ile His Pro
1               5                   10                  15

Lys Asn Ile Gln Ser Leu Glu Val Ile Gly Lys Gly Thr His Cys Asn
                20                  25                  30

Gln Val Glu Val Ile Ala Thr Leu Lys Asp Gly Arg Lys Ile Cys Leu
            35                  40                  45

Asp Pro Asp Ala Pro Arg Ile Lys Lys Ile Val Gln Lys Lys Leu Ala
    50                  55                  60

Gly Asp Glu Ser
65

<210> SEQ ID NO 8
<211> LENGTH: 83
<212> TYPE: PRT
<213> ORGANISM: Unknown
<220> FEATURE:
<223> OTHER INFORMATION: Description of Unknown: Antimicrobial
      polypeptide

<400> SEQUENCE: 8

Asn Leu Ala Lys Gly Lys Glu Glu Ser Leu Asp Ser Asp Leu Tyr Ala
1               5                   10                  15

Glu Leu Arg Cys Met Cys Ile Lys Thr Thr Ser Gly Ile His Pro Lys
                20                  25                  30
```

```
Asn Ile Gln Ser Leu Glu Val Ile Gly Lys Gly Thr His Cys Asn Gln
            35                  40                  45

Val Glu Val Ile Ala Thr Leu Lys Asp Gly Arg Lys Ile Cys Leu Asp
 50                  55                  60

Pro Asp Ala Pro Arg Ile Lys Lys Ile Val Gln Lys Lys Leu Ala Gly
 65                  70                  75                  80

Asp Glu Ser

<210> SEQ ID NO 9
<211> LENGTH: 40
<212> TYPE: PRT
<213> ORGANISM: Unknown
<220> FEATURE:
<223> OTHER INFORMATION: Description of Unknown: Antimicrobial
      polypeptide

<400> SEQUENCE: 9

Tyr Asp Leu Ser Lys Asn Cys Arg Leu Arg Gly Gly Ile Cys Tyr Ile
 1               5                  10                  15

Gly Lys Cys Pro Arg Arg Phe Phe Arg Ser Gly Ser Cys Ser Arg Gly
                20                  25                  30

Asn Val Cys Cys Leu Arg Phe Gly
            35                  40

<210> SEQ ID NO 10
<211> LENGTH: 36
<212> TYPE: PRT
<213> ORGANISM: Unknown
<220> FEATURE:
<223> OTHER INFORMATION: Description of Unknown: Antimicrobial
      polypeptide

<400> SEQUENCE: 10

Glu Lys Lys Cys Pro Gly Arg Cys Thr Leu Lys Cys Gly Lys His Glu
 1               5                  10                  15

Arg Pro Thr Leu Pro Tyr Asn Cys Gly Lys Tyr Ile Cys Cys Val Pro
                20                  25                  30

Val Lys Val Lys
            35

<210> SEQ ID NO 11
<211> LENGTH: 25
<212> TYPE: PRT
<213> ORGANISM: Unknown
<220> FEATURE:
<223> OTHER INFORMATION: Description of Unknown: Antimicrobial
      peptide

<400> SEQUENCE: 11

Gly Val Val Asp Ile Leu Lys Gly Ala Gly Lys Asp Leu Leu Ala His
 1               5                  10                  15

Ala Leu Ser Lys Leu Ser Glu Lys Val
                20                  25

<210> SEQ ID NO 12
<211> LENGTH: 25
<212> TYPE: PRT
<213> ORGANISM: Unknown
<220> FEATURE:
<223> OTHER INFORMATION: Description of Unknown: Antimicrobial
      peptide

<400> SEQUENCE: 12
```

```
Gly Val Leu Asp Ile Leu Lys Gly Ala Gly Lys Asp Leu Leu Ala His
1               5                   10                  15

Ala Leu Ser Lys Ile Ser Glu Lys Val
            20                  25

<210> SEQ ID NO 13
<211> LENGTH: 25
<212> TYPE: PRT
<213> ORGANISM: Unknown
<220> FEATURE:
<223> OTHER INFORMATION: Description of Unknown: Antimicrobial
      peptide

<400> SEQUENCE: 13

Gly Val Leu Asp Ile Leu Thr Gly Ala Gly Lys Asp Leu Leu Ala His
1               5                   10                  15

Ala Leu Ser Lys Leu Ser Glu Lys Val
            20                  25

<210> SEQ ID NO 14
<211> LENGTH: 22
<212> TYPE: PRT
<213> ORGANISM: Unknown
<220> FEATURE:
<223> OTHER INFORMATION: Description of Unknown: Antimicrobial
      peptide

<400> SEQUENCE: 14

Gly Leu Leu Gly Gly Leu Leu Gly Pro Leu Leu Gly Gly Gly Gly Gly
1               5                   10                  15

Gly Gly Gly Gly Leu Leu
            20

<210> SEQ ID NO 15
<211> LENGTH: 29
<212> TYPE: PRT
<213> ORGANISM: Unknown
<220> FEATURE:
<223> OTHER INFORMATION: Description of Unknown: Antimicrobial
      peptide

<400> SEQUENCE: 15

His Asn Lys Gln Glu Gly Arg Asp His Asp Lys Ser Lys Gly His Phe
1               5                   10                  15

His Arg Val Val Ile His His Lys Gly Gly Lys Ala His
            20                  25

<210> SEQ ID NO 16
<211> LENGTH: 12
<212> TYPE: PRT
<213> ORGANISM: Unknown
<220> FEATURE:
<223> OTHER INFORMATION: Description of Unknown: Antimicrobial
      peptide

<400> SEQUENCE: 16

Gly Ile His Asp Ile Leu Lys Tyr Gly Lys Pro Ser
1               5                   10

<210> SEQ ID NO 17
<211> LENGTH: 42
<212> TYPE: PRT
<213> ORGANISM: Unknown
<220> FEATURE:
<223> OTHER INFORMATION: Description of Unknown: Antimicrobial
``` peptide

<400> SEQUENCE: 17

Lys Cys Trp Asn Leu Arg Gly Ser Cys Arg Glu Lys Cys Ile Lys Asn
1               5                   10                  15

Glu Lys Leu Tyr Ile Phe Cys Thr Ser Gly Lys Leu Cys Cys Leu Lys
            20                  25                  30

Pro Lys Phe Gln Pro Asn Met Leu Gln Arg
        35                  40

<210> SEQ ID NO 18
<211> LENGTH: 20
<212> TYPE: PRT
<213> ORGANISM: Unknown
<220> FEATURE:
<223> OTHER INFORMATION: Description of Unknown: Antimicrobial
      peptide

<400> SEQUENCE: 18

Gly Lys Leu Asn Leu Phe Leu Ser Arg Leu Glu Ile Leu Lys Leu Phe
1               5                   10                  15

Val Gly Ala Leu
            20

<210> SEQ ID NO 19
<211> LENGTH: 60
<212> TYPE: PRT
<213> ORGANISM: Unknown
<220> FEATURE:
<223> OTHER INFORMATION: Description of Unknown: Antimicrobial
      polypeptide

<400> SEQUENCE: 19

Gly Ile Trp Ser Ser Ile Lys Asn Leu Ala Ser Lys Ala Trp Asn Ser
1               5                   10                  15

Asp Ile Gly Gln Ser Leu Arg Asn Lys Ala Ala Gly Ala Ile Asn Lys
            20                  25                  30

Phe Val Ala Asp Lys Ile Gly Val Thr Pro Ser Gln Ala Ala Ser Met
        35                  40                  45

Thr Leu Asp Glu Ile Val Asp Ala Met Tyr Tyr Asp
    50                  55                  60

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

His Ser Ser Tyr Trp Tyr Ala Phe Asn Asn Lys Thr Gly Gly Gly Gly
1               5                   10                  15

Leu Leu Arg Ala Ser Ser Val Trp Gly Arg Lys Tyr Tyr Val Asp Leu
            20                  25                  30

Ala Gly Cys Ala Lys Ala
        35

<210> SEQ ID NO 21
<211> LENGTH: 6
<212> TYPE: PRT
<213> ORGANISM: Bombyx mori

```
<400> SEQUENCE: 21

Gly Ser Gly Ala Gly Ala
1               5
```